(12) United States Patent
Bartels et al.

(10) Patent No.: US 11,440,915 B2
(45) Date of Patent: Sep. 13, 2022

(54) TRIAZOLO-AZEPINE DERIVATIVES

(71) Applicant: Hoffmann-La Roche Inc., Little Falls, NJ (US)

(72) Inventors: Bjoern Bartels, Basel (CH); Xinlan Aloise Ford Cook, Oxford (GB); Hasane Ratni, Basel (CH); Michael Reutlinger, Basel (CH); Walter Vifian, Basel (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 141 days.

(21) Appl. No.: 16/954,996

(22) PCT Filed: Dec. 17, 2018

(86) PCT No.: PCT/EP2018/085094
§ 371 (c)(1),
(2) Date: Jun. 17, 2020

(87) PCT Pub. No.: WO2019/121434
PCT Pub. Date: Jun. 27, 2019

(65) Prior Publication Data
US 2020/0317681 A1    Oct. 8, 2020

(30) Foreign Application Priority Data
Dec. 18, 2017 (EP) .................................. 17208057

(51) Int. Cl.
| | | |
|---|---|---|
| *A61K 31/4164* | (2006.01) | |
| *C07D 233/61* | (2006.01) | |
| *C07D 487/04* | (2006.01) | |
| *A61P 25/28* | (2006.01) | |

(52) U.S. Cl.
CPC ............ *C07D 487/04* (2013.01); *A61P 25/28* (2018.01)

(58) Field of Classification Search
CPC .......................... A61K 31/4164; C07D 233/61
USPC ......................................... 514/399; 548/335.5
See application file for complete search history.

(56) References Cited

U.S. PATENT DOCUMENTS

| | | |
|---|---|---|
| 10,941,147 B2 | 9/2021 | Bartels et al. |
| 2021/0395270 A1 | 12/2021 | Ratni et al. |

FOREIGN PATENT DOCUMENTS

| | | | | |
|---|---|---|---|---|
| WO | 2010/083141 A1 | 7/2010 | | |
| WO | 2017/042114 A1 | 3/2017 | | |
| WO | WO-2019121434 A1 | * | 6/2019 | ........... A61K 9/0053 |

OTHER PUBLICATIONS

Jordan, V. C. Nature Reviews: Drug Discovery, 2, 2003, 205.*
Hackam, et al. JAMA, 296(14), 2006, 1731-1732.*
International Preliminary Report on Patentability for PCT/EP2018/085094 dated Jun. 23, 2020.
International Search Report for PCT/EP2018/85094 dated Apr. 4, 2019.

* cited by examiner

*Primary Examiner* — Douglas M Willis
(74) *Attorney, Agent, or Firm* — Genentech, Inc.; Richard G. A. Bone

(57) ABSTRACT

The present invention relates to compounds of formula (I), wherein R is hydrogen or halogen, wherein R may be different if n=2 or 3; n is 1, 2 or 3; (II) is a disubstituted bicyclo[1,1,1]pentane or bicyclo[2,2,2]octane as defined below: (III) or (IV); or to a pharmaceutically active acid addition salt thereof, to a racemic mixture or to its corresponding enantiomer and/or an optical isomer and/or stereoisomer thereof. The compounds may be used for the treatment of Alzheimer's disease, cerebral amyloid angiopathy, hereditary cerebral hemorrhage with amyloidosis, Dutch-type (HCHWA-D), multi-infarct dementia, dementia pugilistica or Down syndrome.

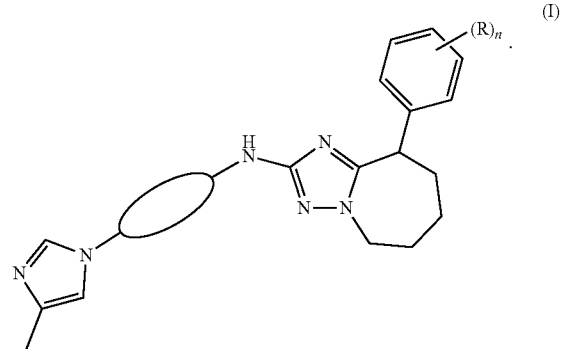

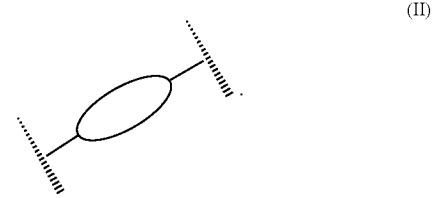

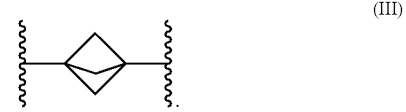

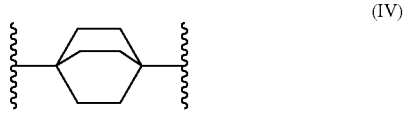

13 Claims, No Drawings

TRIAZOLO-AZEPINE DERIVATIVES

The present invention relates to compounds of formula I,

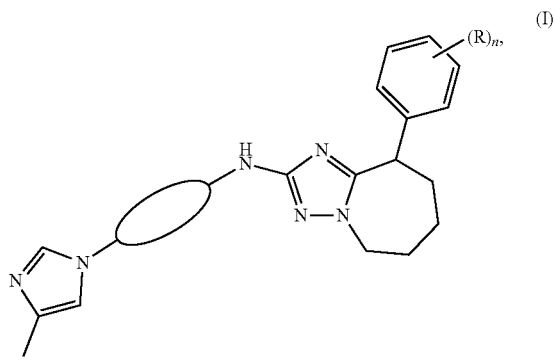

wherein
R is hydrogen or halogen, wherein R may be different if n=2 or 3;
n is 1, 2 or 3;

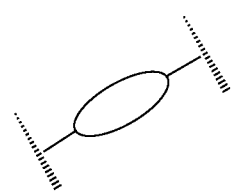

is a disubstituted bicyclo[1,1,1]pentane or bicyclo[2,2,2]octane as defined below

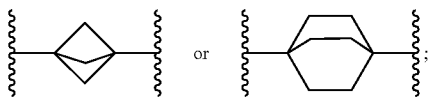 [SMILES: *C12CC(*)(C1)C2 ; *C12CCC(*)(CC1)CC2]

or to a pharmaceutically active acid addition salt thereof, to a racemic mixture or to its corresponding enantiomer and/or an optical isomer and/or stereoisomer thereof.

Now it has been found that the present compounds of formula I are modulators of γ-secretase, they may be useful for the treatment or prevention of a disease associated with the deposition of β-amyloid in the brain, in particular Alzheimer's disease, and other diseases such as cerebral amyloid angiopathy, hereditary cerebral hemorrhage with amyloidosis, Dutch-type (HCHWA-D), multi-infarct dementia, dementia pugilistica and Down syndrome.

Alzheimer's disease (AD) is the most common cause of dementia in later life. Pathologically, AD is characterized by the deposition of amyloid in extracellular plaques and intracellular neurofibrillary tangles in the brain. The amyloid plaques are mainly composed of amyloid peptides (Aβ peptides) which originate from the β-Amyloid Precursor Protein (APP) by a series of proteolytic cleavage steps. Several forms of APP have been identified of which the most abundant are proteins of 695, 751 and 770 amino acids length. They all arise from a single gene through differential splicing. The Aβ peptides are derived from the same domain of the APP.

Aβ peptides are produced from APP through the sequential action of two proteolytic enzymes termed β- and γ-secretase. β-Secretase cleaves first in the extracellular domain of APP just outside of the trans-membrane domain (TM) to produce a C-terminal fragment of APP (CTFP) containing the TM- and cytoplasmatic domain. CTFP is the substrate for γ-secretase which cleaves at several adjacent positions within the TM to produce the Aβ peptides and the cytoplasmic fragment. Various proteolytic cleavages mediated by γ-secretase result in Aβ peptides of different chain length, e.g. Aβ38, Aβ40 and Aβ42. The latter one is regarded to be the more pathogenic amyloid peptide because of its strong tendency to form neurotoxic aggregates.

The β-secretase is a typical aspartyl protease. The γ-secretase is a high molecular weight complex that consists of four essential subunits: Presenilin (PS, including PS1 and PS2), nicastrin, anterior pharynx defective 1 (APH-1), and presenilin enhancer 2 (PEN-2). The atomic structure of human γ-secretase at 3.4 Å resolution has been published (X. Bai, C. Yan, G. Yang, P. Lu, D. Ma, L. Sun, R. Zhou, S. H. W. Scheres, Y. Shi, Nature 2015, 525, pages 212-217). The presenilins are bearing the catalytic site and represent a group of atypical aspartyl proteases which cleave their substrates within the TM of and which are themselves polytopic membrane proteins. The other essential components of γ-secretase, nicastrin and the products of the aph1 and pen-2 genes are believed to be responsible for substrate recognition and recruitment. Proven substrates for γ-secretase are APP and the proteins of the Notch receptor family, however, γ-secretase has a loose substrate specificity and many further membrane proteins unrelated to APP and Notch have been reported to be cleaved by the γ-secretase in vitro.

The γ-secretase activity is absolutely required for the production of Aβ peptides. This has been shown both by genetic means, i.e., ablation of the presenilin genes and by low-molecular-weight inhibitory compounds. According to the amyloid cascade hypothesis for AD the production and deposition of Aβ is the ultimate cause for the disease. Therefore, it was believed that selective and potent inhibition of γ-secretase might be useful for the prevention and treatment of AD.

An alternative mode of treatment is the modulation of the γ-secretase activity which results in a selective reduction of the Aβ42 production. This will lead in an increase of shorter Aβ isoforms, such as Aβ38, Aβ37 or others, which have no or reduced capability for aggregation and plaque formation, and are not or less neurotoxic. Compounds which show this effect on modulating γ-secretase activity include certain non-steroidal anti-inflammatory drugs (NSAIDs) and related analogues (Weggen et al., Nature, 414 (2001) 212-16).

Thus, the compounds of this invention will be useful for the treatment or prevention of a disease associated with the deposition of β-amyloid in the brain, in particular Alzheimer's disease, and other diseases such as cerebral amyloid angiopathy, hereditary cerebral hemorrhage with amyloidosis, Dutch-type (HCHWA-D), multi-infarct dementia, dementia pugilistica and Down syndrome.

Numerous documents describe the current knowledge on γ-secretase modulation, for example the following publications:
Morihara et al, J. Neurochem., 83 (2002) 1009-12
Jantzen et al, J. Neuroscience, 22 (2002) 226-54
Takahashi et al, J. Biol. Chem., 278 (2003) 18644-70
Beher et al, J. Biol. Chem., 279 (2004) 43419-26
Lleo et al, Nature Med., 10 (2004) 1065-6
Kukar et al, Nature Med., 11 (2005) 545-50

Perretto et al, J. Med. Chem. 48 (2005) 5705-20
Clarke et al, J. Biol. Chem., 281 (2006) 31279-89
Stock et al, Bioorg. Med. Chem. Lett. 16 (2006) 2219-2223
Narlawar et al, J. Med. Chem. 49 (2006) 7588-91
Ebke et al, J. Biol. Chem., 286 (2011) 37181-86
Oehlich, Gijsen et al, J. Med. Chem., 54 (2011), 669-698
Li et al., Biochemistry, 52 (2013), 3197-3216
Hall et al, Progress in Med. Chem., 53 (2014) 101-145
Bursavich et al, J. Med. Chem., 59 (2016) 7389-7409

The following definitions for compounds of formula I are used:

The term "halogen" denotes chlorine, iodine, fluorine and bromine.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like.

Objects of the present invention are compounds of formula I, the use of such compounds for the treatment of Alzheimer's disease, cerebral amyloid angiopathy, hereditary cerebral hemorrhage with amyloidosis, Dutch-type (HCHWA-D), multi-infarct dementia, dementia pugilistica or Down syndrome, their manufacture and medicaments based on a compound of formula I in accordance with the invention.

Further objects of the present invention are all forms of optically pure enantiomers, racemates or diastereometric mixtures for compounds of formula I.

One object of the present invention is a compound of formula I-a,

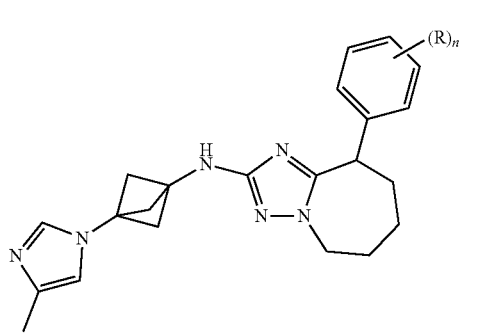

I-a wherein
R is hydrogen or halogen, wherein R may be different if n=2 or 3;
n is 1, 2 or 3;
or a pharmaceutically active acid addition salt thereof, a racemic mixture or its corresponding enantiomer and/or an optical isomer and/or stereoisomer thereof, for example the following compounds:
(9R)-9-(3-chlorophenyl)-N-[3-(4-methylimidazol-1-yl)-1-bicyclo[1.1.1]pentanyl]-6,7,8,9-tetrahydro-5H-[1,2,4]triazolo[1,5-a]azepin-2-amine
(9S)-9-(3-chlorophenyl)-N-[3-(4-methylimidazol-1-yl)-1-bicyclo[1.1.1]pentanyl]-6,7,8,9-tetrahydro-5H-[1,2,4]triazolo[1,5-a]azepin-2-amine
(9R)-9-(4-fluorophenyl)-N-[3-(4-methylimidazol-1-yl)-1-bicyclo[1.1.1]pentanyl]-6,7,8,9-tetrahydro-5H-[1,2,4]triazolo[1,5-a]azepin-2-amine
(9S)-9-(4-fluorophenyl)-N-[3-(4-methylimidazol-1-yl)-1-bicyclo[1.1.1]pentanyl]-6,7,8,9-tetrahydro-5H-[1,2,4]triazolo[1,5-a]azepin-2-amine
(9R)-9-(4-chlorophenyl)-N-[3-(4-methylimidazol-1-yl)-1-bicyclo[1.1.1]pentanyl]-6,7,8,9-tetrahydro-5H-[1,2,4]triazolo[1,5-a]azepin-2-amine
(9S)-9-(4-chlorophenyl)-N-[3-(4-methylimidazol-1-yl)-1-bicyclo[1.1.1]pentanyl]-6,7,8,9-tetrahydro-5H-[1,2,4]triazolo[1,5-a]azepin-2-amine
(9R)-9-(3-chloro-5-fluoro-phenyl)-N-[3-(4-methylimidazol-1-yl)-1-bicyclo[1.1.1]pentanyl]-6,7,8,9-tetrahydro-5H-[1,2,4]triazolo[1,5-a]azepin-2-amine
(9S)-9-(3-chloro-5-fluoro-phenyl)-N-[3-(4-methylimidazol-1-yl)-1-bicyclo[1.1.1]pentanyl]-6,7,8,9-tetrahydro-5H-[1,2,4]triazolo[1,5-a]azepin-2-amine
(9R)-9-(3,4-difluorophenyl)-N-[3-(4-methylimidazol-1-yl)-1-bicyclo[1.1.1]pentanyl]-6,7,8,9-tetrahydro-5H-[1,2,4]triazolo[1,5-a]azepin-2-amine
(9S)-9-(3,4-difluorophenyl)-N-[3-(4-methylimidazol-1-yl)-1-bicyclo[1.1.1]pentanyl]-6,7,8,9-tetrahydro-5H-[1,2,4]triazolo[1,5-a]azepin-2-amine
(9R)-9-(2-fluorophenyl)-N-[3-(4-methylimidazol-1-yl)-1-bicyclo[1.1.1]pentanyl]-6,7,8,9-tetrahydro-5H-[1,2,4]triazolo[1,5-a]azepin-2-amine
(9S)-9-(2-fluorophenyl)-N-[3-(4-methylimidazol-1-yl)-1-bicyclo[1.1.1]pentanyl]-6,7,8,9-tetrahydro-5H-[1,2,4]triazolo[1,5-a]azepin-2-amine
(9R)-N-[3-(4-methylimidazol-1-yl)-1-bicyclo[1.1.1]pentanyl]-9-(2,3,4-trifluorophenyl)-6,7,8,9-tetrahydro-5H-[1,2,4]triazolo[1,5-a]azepin-2-amine or
(9S)-N-[3-(4-methylimidazol-1-yl)-1-bicyclo[1.1.1]pentanyl]-9-(2,3,4-trifluorophenyl)-6,7,8,9-tetrahydro-5H-[1,2,4]triazolo[1,5-a]azepin-2-amine.

One object of the present invention is a compound of formula I-b,

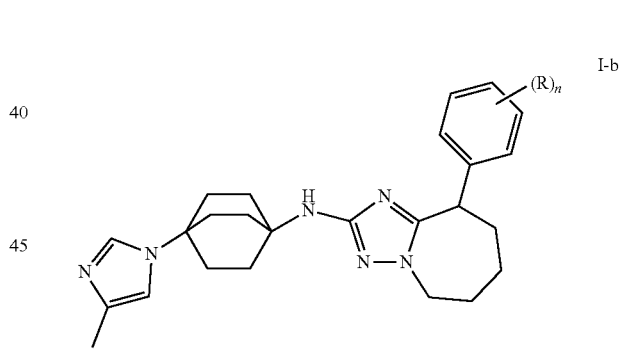

I-b wherein
R is hydrogen or halogen, wherein R may be different if n=2 or 3;
n is 1, 2 or 3;
or a pharmaceutically active acid addition salt thereof, a racemic mixture or its corresponding enantiomer and/or an optical isomer and/or stereoisomer thereof, for example the following compounds:
(9R)-9-(3-chloro-5-fluoro-phenyl)-N-[4-(4-methylimidazol-1-yl)-1-bicyclo[2.2.2]octanyl]-6,7,8,9-tetrahydro-5H-[1,2,4]triazolo[1,5-a]azepin-2-amine
(9S)-9-(3-chloro-5-fluoro-phenyl)-N-[4-(4-methylimidazol-1-yl)-1-bicyclo[2.2.2]octanyl]-6,7,8,9-tetrahydro-5H-[1,2,4]triazolo[1,5-a]azepin-2-amine
(9R)-9-(3,4-difluorophenyl)-N-[4-(4-methylimidazol-1-yl)-1-bicyclo[2.2.2]octanyl]-6,7,8,9-tetrahydro-5H-[1,2,4]triazolo[1,5-a]azepin-2-amine (9S)-9-(3,4-difluorophenyl)-N-[4-(4-methylimidazol-1-yl)-1-bicyclo[2.2.2]octanyl]-6,7,8,9-tetrahydro-5H-[1,2,4]triazolo[1,5-a]azepin-2-amine (9R)-9-(2-fluorophenyl)-N-[4-(4-methylimidazol-1-yl)-1-bicyclo[2.2.2]octanyl]-6,7,8,9-tetrahydro-5H-[1,2,4]triazolo[1,5-a]azepin-2-amine (9S)-9-(2-fluorophenyl)-N-[4-(4-methylimidazol-1-yl)-1-bicyclo[2.2.2]octanyl]-6,7,8,9-tetrahydro-5H-[1,2,4]triazolo[1,5-a]azepin-2-amine (9R)-N-[4-(4-methylimidazol-1-yl)-1-bicyclo[2.2.2]octanyl]-9-(2,3,4-trifluorophenyl)-6,7,8,9-tetrahydro-5H-[1,2,4]triazolo[1,5-a]azepin-2-amine or (9S)-N-[4-(4-methylimidazol-1-yl)-1-bicyclo[2.2.2]octanyl]-9-(2,3,4-trifluorophenyl)-6,7,8,9-tetrahydro-5H-[1,2,4]triazolo[1,5-a]azepin-2-amine.

The present compounds of formula I and their pharmaceutically acceptable salts can be prepared by methods known in the art, for example, by processes described below, which process comprises a) reacting a compound of formula 7

7 with a compound of formula 8

8 to a compound of formula I

I wherein the substituents have the meaning as described above, and, if desired, converting the compounds obtained into pharmaceutically acceptable acid addition salts, or b) cyclizing a compound of formula 14

14

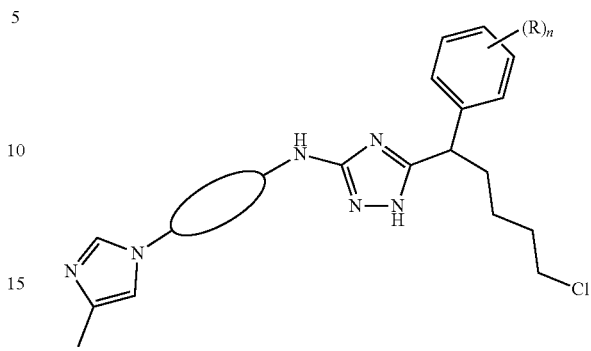

in the presence of KI and $K_2CO_3$ to a compound of formula I

I

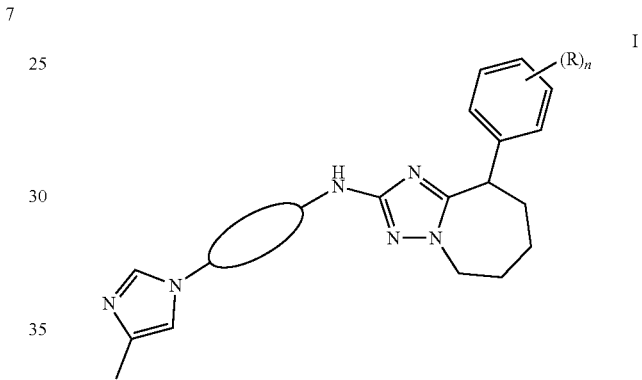

wherein the substituents have the meaning as described above, and, if desired, converting the compounds obtained into pharmaceutically acceptable acid addition salts.

In more detail, compounds of formula I and their intermediates may be prepared by schemes 1 and 2 and by the description of 22 specific examples.

General Synthesis of Derivatives I

Scheme 1

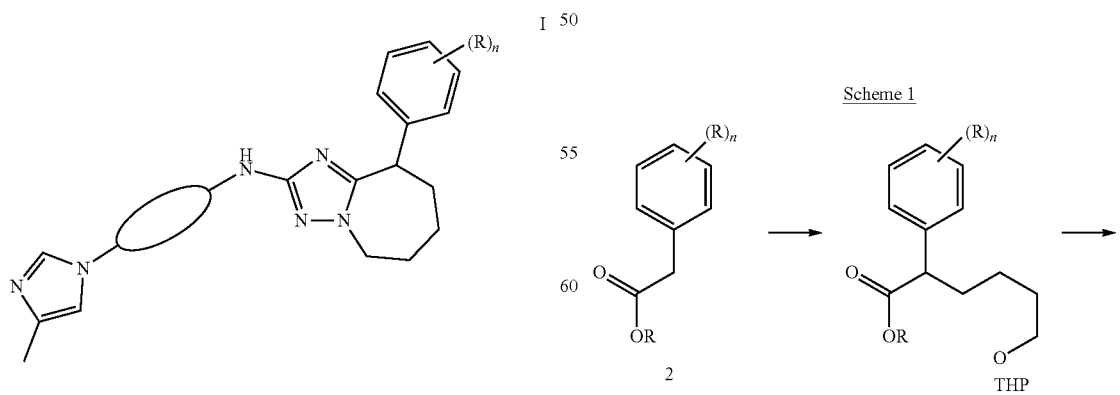

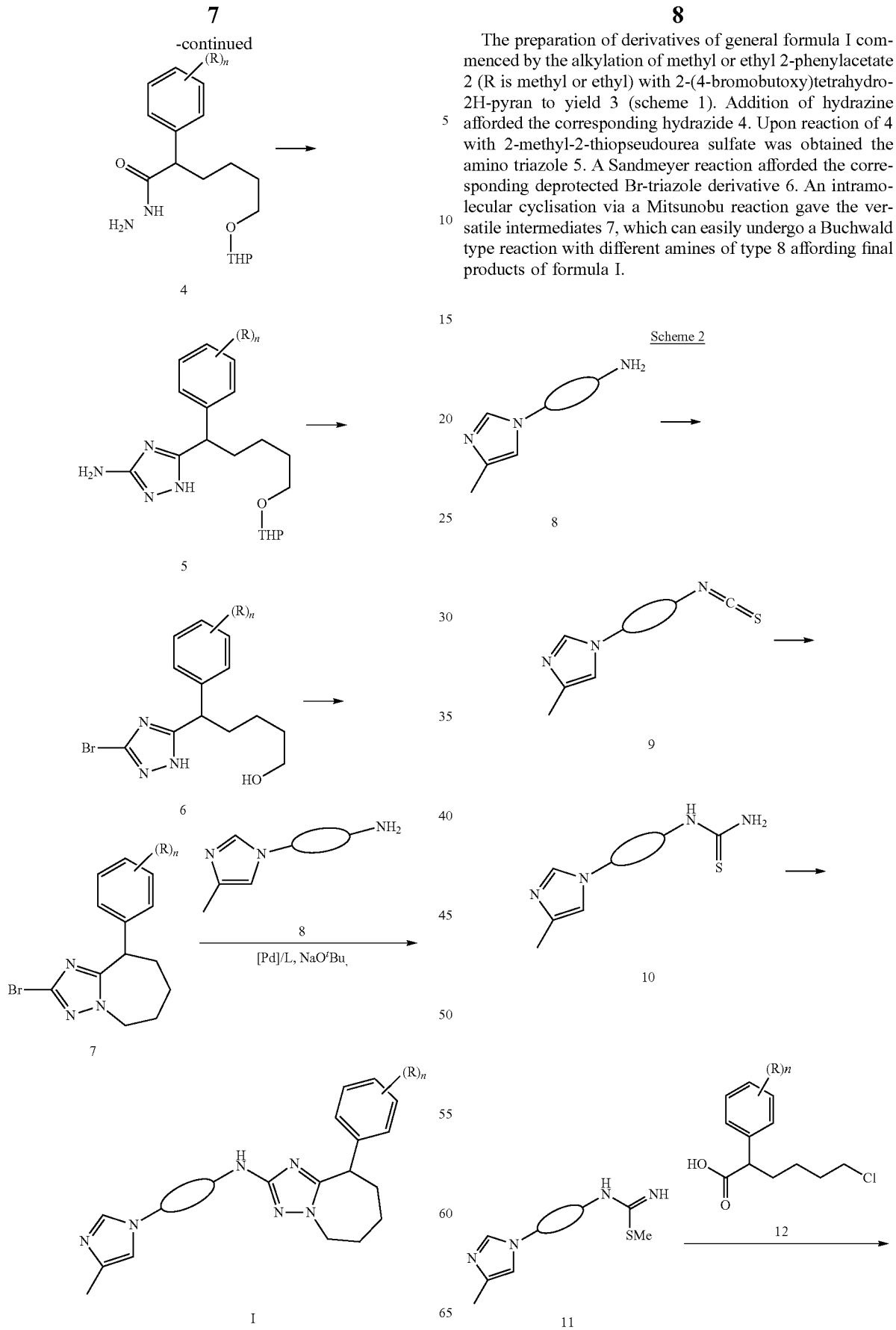

The preparation of derivatives of general formula I commenced by the alkylation of methyl or ethyl 2-phenylacetate 2 (R is methyl or ethyl) with 2-(4-bromobutoxy)tetrahydro-2H-pyran to yield 3 (scheme 1). Addition of hydrazine afforded the corresponding hydrazide 4. Upon reaction of 4 with 2-methyl-2-thiopseudourea sulfate was obtained the amino triazole 5. A Sandmeyer reaction afforded the corresponding deprotected Br-triazole derivative 6. An intramolecular cyclisation via a Mitsunobu reaction gave the versatile intermediates 7, which can easily undergo a Buchwald type reaction with different amines of type 8 affording final products of formula I.

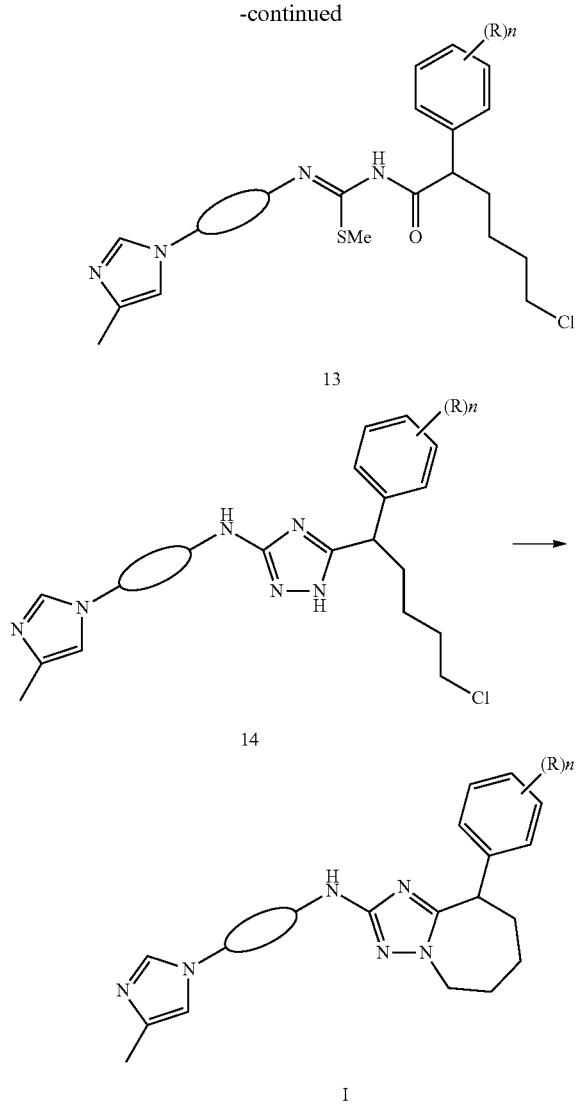

Alternatively, compounds of general formula I could be prepared in the following manner (scheme 2). The aminopiperidine 8 was converted into the corresponding isothiocyanato derivatives 9 upon reaction with 1,1'-thiocarbonyl-dipyridin-2(1H)-one. Addition of ammonia gave the thioureas 10 which can udergoes a S alkylation with MeI providing 11. An amid coupling with intermediates of formula 12 gave 13, which was readily converted into the triazole derivatives 14 upon reaction with hydrazine. Finally, an intramolecular cyclisation in the presence of KI and $K_2CO_3$ afforded compounds of formula I.

The compounds were investigated in accordance with the test given hereinafter.

Description of γ-Secretase Assay

Cellular γ-Secretase Assay

Human neuroglioma H4 cells overexpressing human APP695 with the Swedish double mutation (K595N/M596L) were plated at 30,000 cells/well/100 μl in 96-well plates in IMDM media containing 10% FCS, 0.2 mg/l Hygromycin B and incubated at 37° C., 5% $CO_2$.

3-4 hr post plating, compounds are a diluted in media and 50 μl is added as 1.5-fold concentrate to achieve the final concentration. Compound incubation is performed for 24 hr. Final doses typically range from 4 μM down to 0.001 μM in half-log steps resulting in a eight point dose response curve.

Appropriate controls using vehicle only and reference compound were applied to this assay. The final concentration of $Me_2SO$ was 0.4%.

After incubation at 37° C., 5% $CO_2$, the supernatant was subjected to quantification of secreted Aβ42 by the means of an AlphaLisa assay kit (Human Amyloid beta 1-42 Kit: Cat #AL203C, Perkin Elmer). 20 μl of the cell culture supernatant was transferred to an assay plate. Then 10 μl of a mixture of the AlphaLisa coupled capture antibody and the biotinylated detection antibody was added and incubated for 3 hours at room temperature while softly shaking the assay plate. After a further addition of 20 μl of the Donor beads the assay plate was incubated for 30 min at room temperature and constant shaking without exposure to direct light. The assay plate was then read on a Paradigm AlphaLisa Reader using the build-in program with excitation at 680 nm and emission at 570 nm.

The measured signals were then used to calculate $IC_{50}$ values for inhibition of Aβ42 secretion by nonlinear regression fit analysis using XLfit 5.3 software (IDBS).

The table below shows the data for all compounds for the inhibition of Aβ42 secretion (uM):

| Example No. | $EC_{50}$ Aβ42 (uM) | Example No. | $EC_{50}$ Aβ42 (uM) |
| --- | --- | --- | --- |
| 1 | 0.015 | 2 | 0.016 |
| 3 | 0.025 | 4 | 0.031 |
| 5 | 0.026 | 6 | 0.023 |
| 7 | 0.015 | 8 | 0.014 |
| 9 | 0.008 | 10 | 0.014 |
| 11 | 0.039 | 12 | 0.049 |
| 13 | 0.044 | 14 | 0.027 |
| 15 | 0.038 | 16 | 0.019 |
| 17 | 0.056 | 18 | 0.062 |
| 19 | 0.014 | 20 | 0.010 |
| 21 | 0.043 | 22 | 0.027 |

The compounds of formula I and the pharmaceutically acceptable salts of the compounds of formula I can be used as medicaments, e.g. in the form of pharmaceutical preparations. The pharmaceutical preparations can be administered orally, e.g. in the form of tablets, coated tablets, dragées, hard and soft gelatine capsules, solutions, emulsions or suspensions. The administration can, however, also be effected rectally, e.g. in the form of suppositories, parenterally, e.g. in the form of injection solutions. The administration can also be effected topically, e.g. transdermal administration, or in form of eye drops or ear drops.

The compounds of formula I can be processed with pharmaceutically inert, inorganic or organic carriers for the production of pharmaceutical preparations. Lactose, corn starch or derivatives thereof, talc, stearic acids or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like. Depending on the nature of the active substance no carriers are, however, usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical preparations can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

Medicaments containing a compound of formula I or a pharmaceutically acceptable salt thereof and a therapeutically inert carrier are also an object of the present invention, as is a process for their production, which comprises bringing one or more compounds of formula I and/or pharmaceutically acceptable acid addition salts and, if desired, one or more other therapeutically valuable substances into a galenical administration form together with one or more therapeutically inert carriers.

In accordance with the invention compounds of formula I as well as their pharmaceutically acceptable salts are useful in the control or prevention of illnesses based on the inhibition of Aβ42 secretion, such as of Alzheimer's disease.

The dosage can vary within wide limits and will, of course, have to be adjusted to the individual requirements in each particular case. In the case of oral administration the dosage for adults can vary from about 0.01 mg to about 1000 mg per day of a compound of general formula I or of the corresponding amount of a pharmaceutically acceptable salt thereof. The daily dosage may be administered as single dose or in divided doses and, in addition, the upper limit can also be exceeded when this is found to be indicated.

| Tablet Formulation (Wet Granulation) | | | | | |
|---|---|---|---|---|---|
| | | | mg/tablet | | |
| Item | Ingredients | 5 | 25 | 100 | 500 |
| 1. | Compound of formula I | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure
1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

| Capsule Formulation | | | | | |
|---|---|---|---|---|---|
| | | | mg/capsule | | |
| Item | Ingredients | 5 | 25 | 100 | 500 |
| 1. | Compound of formula I | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure
1. Mix items 1, 2 and 3 in a suitable mixer for 30 minutes.
2. Add items 4 and 5 and mix for 3 minutes.
3. Fill into a suitable capsule.

EXPERIMENTAL PART

The following examples are provided for illustration of the invention. They should not be considered as limiting the scope of the invention, but merely as being representative thereof.

General

Analytical Methods

HPLC (method LCMS_fastgradient)

Column: Agilent Zorbax Eclipse Plus C18, Rapid Resolution HT, 2.1×30 mm, 1.8 m, Part. no. 959731-902

Solvent A: Water 0.01% Formic Acid; Solvent B: acetonitrile (MeCN)

Gradients:

| Time [min] | Flow Rate [ml/min] | % A | % B |
|---|---|---|---|
| Initial | 0.8 | 97 | 3 |
| 0.2 | 1.0 | 97 | 3 |
| 1.7 | 1.0 | 3 | 97 |
| 2.0 | 1.0 | 3 | 97 |
| 2.1 | 1.0 | 97 | 3 |

Abbreviations

The following abbreviations were used in the experimental part:

THF=tetrahydrofuran;

MTBE=methyl-tert-butylether;

DMF=dimethylformamide;

TLC=thin layer chromatography;

rt=room temperature, 20-25° C.

General Synthesis of Intermediates 12

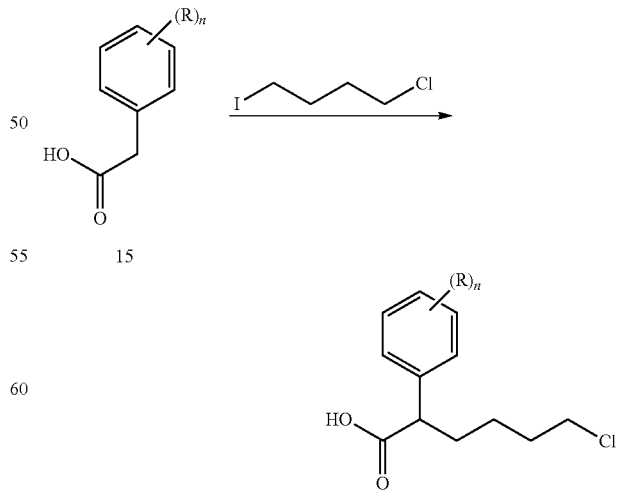

Intermediates 12 were readily prepared upon alkylation of commercially available acids 15 with 1-chloro-4-iodo-butane in the presence of a base (e.g. NaHMDS) at low temperature.

Intermediates of Type 7

Intermediate 7-1

2-bromo-9-(2,3,4-trifluorophenyl)-6,7,8,9-tetrahydro-5H-[1,2,4]triazolo[1,5-a]azepine

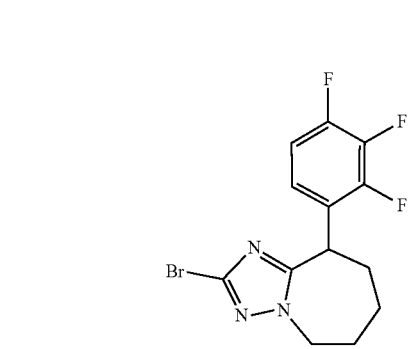

7-1

Step 1: methyl 6-tetrahydropyran-2-yloxy-2-(2,3,4-trifluorophenyl)hexanoate

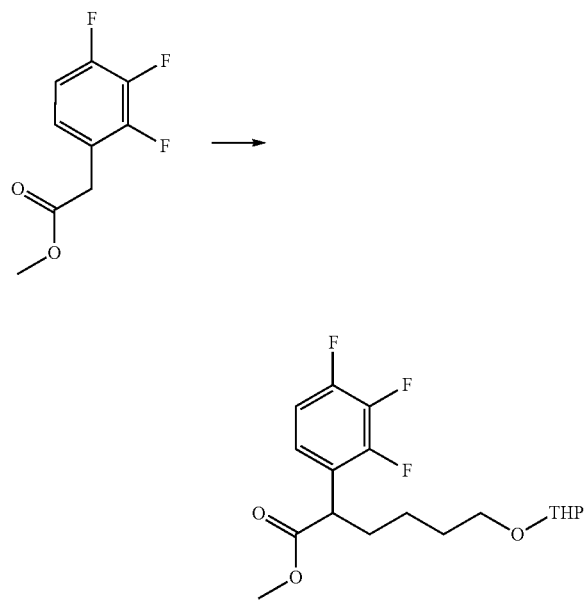

To a stirred solution of methyl 2-(2,3,4-trifluorophenyl) acetate (5.10 g, 25 mmol) in DMF (40 ml) at 0° C. was added NaH (60%, 1.10 g, 27.5 mmol). The reaction mixture was stirred for 1 hour and then canuulated dropwise into a solution of 2-(4-bromobutoxy)tetrahydropyran (5.92 g, 25 mmol) in DMF (40 mL) also at 0° C. The reaction was further stirred at RT for one hour and poured onto an aqueous saturated solution of $NH_4Cl$. The product was extracted with EtOAc, and the combined organic phase was dried over $Na_2SO_4$ and concentrated under vacuo. A column chromatography ($SiO_2$, Heptane/EtOAc) gave 6.07 g (67%) of methyl 6-tetrahydropyran-2-yloxy-2-(2,3,4-trifluorophenyl)hexanoate as a light yellow oil.

Step 2: 6-tetrahydropyran-2-yloxy-2-(2,3,4-trifluorophenyl)hexanehydrazide

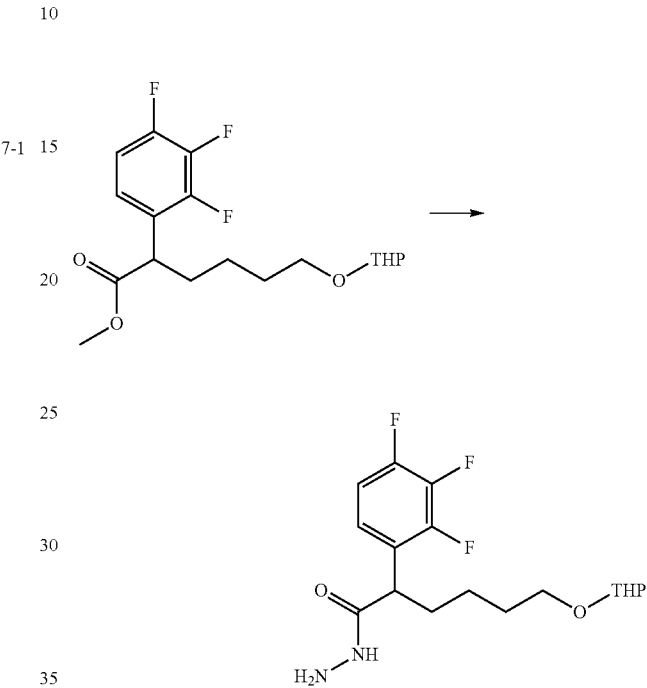

To a stirred solution of methyl 6-tetrahydropyran-2-yloxy-2-(2,3,4-trifluorophenyl)hexanoate (6.07 g, 16.8 mmol) in MeOH (56 mL) was added hydrazine hydrate (14.1 mL, 219 mmol). The reaction mixture was stirred at 80° C. for 17 hours and concentrated under vacuo. The residue was diluted with water and the product extracted with EtOAc. The combined organic phase was dried over $Na_2SO_4$ and concentrated under vacuo to give 6.10 g (99%) of 6-tetrahydropyran-2-yloxy-2-(2,3,4-trifluorophenyl)hexanehydrazide as a colorless oil. MS (ES+) m/z: 361.2 [$(M+H)^+$].

Step 3: 5-[5-tetrahydropyran-2-yloxy-1-(2,3,4-trifluorophenyl)pentyl]-4H-1,2,4-triazol-3-amine

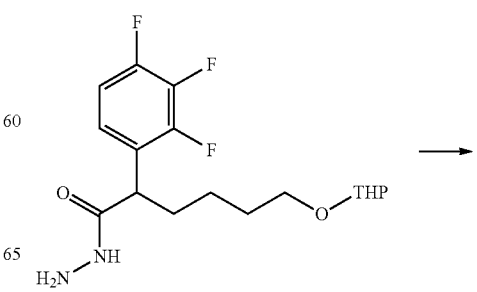

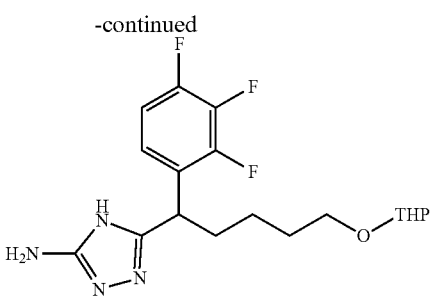

In a sealed reactor, 6-tetrahydropyran-2-yloxy-2-(2,3,4-trifluorophenyl)hexanehydrazide (6.10 g, 16.9 mmol) was dissolved in 2-propanol (44 mL). Et₃N (5.1 mL, 50.8 mmol) and 2-methyl-2-thiopseudourea sulfate (2.36 g, 8.46 mmol) were added and the reaction mixture was heated at 130° C. over night. The reaction mixture was then cooled to RT, concentrated under vacuo and the residue diluted with CH₂Cl₂ and then washed with brine. The organic phase was dried over Na₂SO₄, concentrated under vacuo. A column chromatography (SiO₂, CH₂Cl₂/MeOH) gave (4.2 g, 65%) of 5-[5-tetrahydropyran-2-yloxy-1-(2,3,4-trifluorophenyl)pentyl]-4H-1,2,4-triazol-3-amine as a white foam. MS (ES+) m/z: 385.2 [(M+H)⁺].

Step 4:5-(5-bromo-4H-1,2,4-triazol-3-yl)-5-(2,3,4-trifluorophenyl)pentan-1-ol

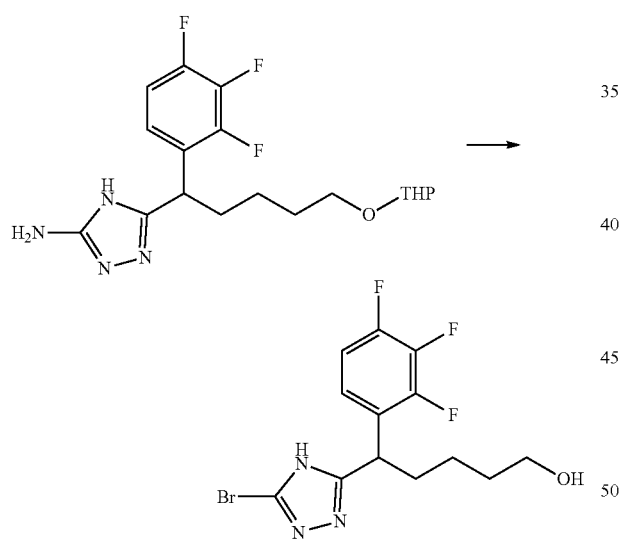

To a black solution of tert-butyl nitrite (1.88 g, 2.17 mL, 16.4 mmol) and cupric bromide (3.66 g, 16.4 mmol) in CH₃CN (35 mL) at 60° C. was added portion wise 5-[5-tetrahydropyran-2-yloxy-1-(2,3,4-trifluorophenyl)pentyl]-4H-1,2,4-triazol-3-amine (4.20 g, 10.9 mmol). The reaction mixture was then heated at 75° C. for one hour and cooled down to RT. HCl 2N (3 mL) was added and stirring was continued 30 minutes. The reaction mixture was concentrated under vacuo, and the residue diluted with EtOAc and washed with water. The organic phase was dried over Na₂SO₄, concentrated under vacuo. A column chromatography (SiO₂, Heptane/EtOAc) gave 2.15 g (54%) of 5-(5-bromo-4H-1,2,4-triazol-3-yl)-5-(2,3,4-trifluorophenyl)pentan-1-ol as a yellow foam. MS (ES+) m/z: 364.1 [(M+H)⁺].

Step 5:2-bromo-9-(2,3,4-trifluorophenyl)-6,7,8,9-tetrahydro-5H-[1,2,4]triazolo[1,5-a]azepine

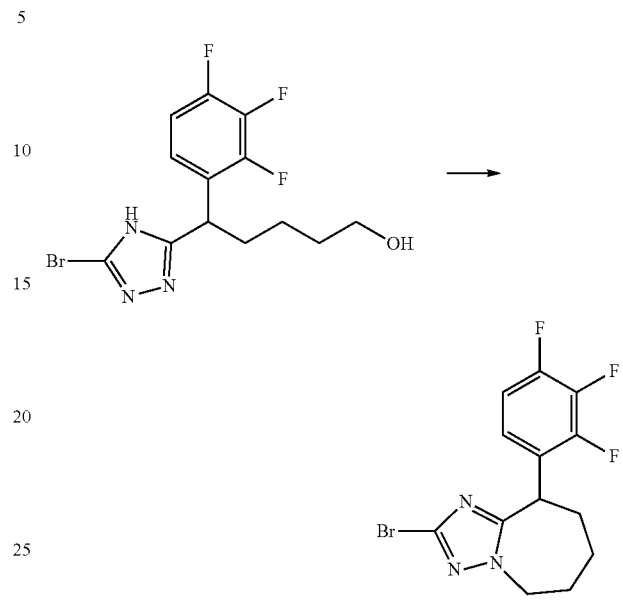

To a solution of 5-(5-bromo-4H-1,2,4-triazol-3-yl)-5-(2,3,4-trifluorophenyl)pentan-1-ol (2.09 g, 5.74 mmol) and triphenylphosphine (2.26 g, 8.61 mmol) in THF (64 mL) at −10° C. was added DEAD (1.36 mL, 8.61 mmol). The reaction mixture was further stirred for 30 minutes at this temperature and then poured into water. The product was extracted with EtOAc and the combined organic phase was dried over Na₂SO₄ and concentrated under vacuo. A column chromatography (SiO₂, Heptane/EtOAc) gave 0.56 g (28%) of 2-bromo-9-(2,3,4-trifluorophenyl)-6,7,8,9-tetrahydro-5H-[1,2,4]triazolo[1,5-a]azepine (7.1) as white solid. MS (ES+) m/z: 347.1 [(M+H)⁺].

Intermediate 7-2

2-bromo-9-(3-chloro-5-fluoro-phenyl)-6,7,8,9-tetrahydro-5H-[1,2,4]triazolo[1,5-a]azepine 7-2

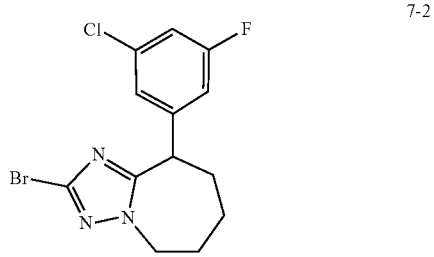 [SMILES: Fc1cc(Cl)cc(C2CCCCn3nc(Br)nc32)c1]

In analogy to the preparation of the intermediate 7.1, starting from methyl 2-(3-chloro-5-fluoro-phenyl)acetate was prepared the intermediate 2-bromo-9-(3-chloro-5-fluoro-phenyl)-6,7,8,9-tetrahydro-5H-[1,2,4]triazolo[1,5-a]azepine (7.2) as a white solid. MS (ES+) m/z: 344.1/346.1 [(M+H)⁺].

Intermediate 7-3

2-bromo-9-(3,4-difluorophenyl)-6,7,8,9-tetrahydro-5H-[1,2,4]triazolo[1,5-a]azepine

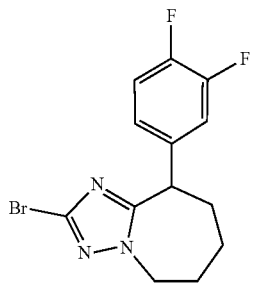

7-3

In analogy to the preparation of the intermediate 7.1, starting from methyl 2-(3,4-difluorophenyl)acetate was prepared the intermediate 2-bromo-9-(3,4-difluorophenyl)-6,7,8,9-tetrahydro-5H-[1,2,4]triazolo[1,5-a]azepine (7.3) as a white solid. MS (ES+) m/z: 346.2/348.2 [(M+H)$^+$].

Intermediate 7-4

2-bromo-9-(2-fluorophenyl)-6,7,8,9-tetrahydro-5H-[1,2,4]triazolo[1,5-a]azepine

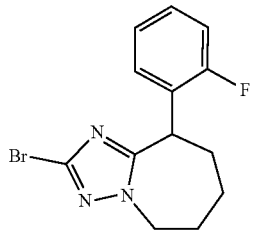

7-4

In analogy to the preparation of the intermediate 7.1, starting from methyl 2-(2-fluorophenyl)acetate was prepared the intermediate 2-bromo-9-(2-fluorophenyl)-6,7,8,9-tetrahydro-5H-[1,2,4]triazolo[1,5-a]azepine (7.4) as a white solid. MS (ES+) m/z: 310.2/312.2 [(M+H)$^+$].

Intermediates of Type 8

Intermediate 8-1

3-(4-methylimidazol-1-yl)bicyclo[1.1.1]pentan-1-amine

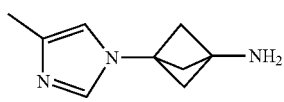

8-1

Step 1: tert-butyl N-[3-(acetonylamino)-1-bicyclo[1.1.1]pentanyl]carbamate

Potassium iodide (0.15 g, 0.92 mmol) and cesium carbonate (1.50 g, 4.61 mmol) were added to tert-butyl N-(3-amino-1-bicyclo[1.1.1]pentanyl)carbamate (0.96 g, 4.61 mmol) in solution in DMF (20 mL). The mixture was cooled to 0° C. and 1-chloropropan-2-one (0.49 g, 5.07 mmol) in solution in DMF (5 mL) was added. Stirring was continued overnight while the temperature was raising to RT. The mixture was filtered, and concentrated under vacuo. Column chromatography (1% to 10% MeOH in TBME) gave the title compound (0.68 g, 58%) as a light brown foam. MS (ES+) m/z 255.2 [M+H].

Step 2: tert-butyl N-[3-[acetonyl(formyl)amino]-1-bicyclo[1.1.1]pentanyl]carbamate Acetic anhydride (1.01 g, 0.93 mL, 9.88 mmol) was added to formic acid (1.79 g, 1.50 mL, 39 mmol) and stirred for 1 hour. A solution of tert-butyl N-[3-(acetonylamino)-1-bicyclo[1.1.1]pentanyl]carbamate (0.66 g, 2.60 mmol) in THF (12 mL) was added. The resulting dark solution was stirred for 30 minutes and then poured into H$_2$O (30 mL). EtOAc (50 mL) was added and the biphase mixture was stirred and the pH adjusted to 8-9 by addition of NaHCO$_3$ in small portions. The organic phase was then separated, dried over Na$_2$SO$_4$ and concentrated under vacuo. A column chromatography (30% to 100% EtOAc in Heptane) gave the title compound (0.33 g, 45%) as a brown foam. MS (ES+) m/z 283.1 [M+H].

Step 3: tert-butyl N-[3-(4-methylimidazol-1-yl)-1-bicyclo[1.1.1]pentanyl]carbamate To a solution of tert-butyl N-[3-[acetonyl(formyl)amino]-1-bicyclo[1.1.1]pentanyl]carbamate (0.33 g, 1.17 mmol) in acetic acid (4 mL) was added ammonium acetate (0.45 g, 5.84 mmol). The reaction mixture was heated at 100° C. for 10 hours before a second portion of ammonium acetate (0.45 g, 5.84 mmol) was added and stirring continued for an other 4 hours. The volatiles were removed under vacuo, and a column chromatography (3% to 50% 2N NH/MeOH in TBME) gave the title product (0.096 g, 31%) as an off-white solid which was used directly in the next step.

Step 4: 3-(4-methylimidazol-1-yl)bicyclo[1.1.1]pentan-1-amine

To a solution of tert-butyl N-[3-(4-methylimidazol-1-yl)-1-bicyclo[1.1.1]pentanyl]carbamate (0.096 g, 0.365 mmol) in CH$_2$Cl$_2$ (2 mL) was added TFA (0.88 g, 0.60 mL, 7.78 mmol) and the mixture stirred overnight at RT. The volatiles were removed under vacuo, the residue redissolved in MeOH (2 mL) and an aqueous solution of NH$_4$OH (25%, 0.5 mL) followed by diatomaceous earth material isolute HM-N (3 g) were added. The mixture was concentrated and a column chromatography (2% to 15% of 2N NH$_3$/MeOH in CH$_2$Cl$_2$) gave the title product (0.032 g, 16%) as a viscous colorless oil. MS (ES+) m/z 164.1 [M+H].

Intermediate 8-2

4-(4-methylimidazol-1-yl)bicyclo[2.2.2]octan-1-amine. hydrochloride

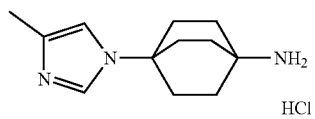

8-2

Step 1: tert-butyl N-[4-(acetonylamino)-1-bicyclo[2.2.2]octanyl]carbamate

Potassium iodide (0.13 g, 0.78 mmol) and cesium carbonate (3.82 g, 11.7 mmol) were added to tert-butyl N-(4-amino-1-bicyclo[2.2.2]octanyl)carbamate (0.94 g, 3.91 mmol) in solution in DMF (6 mL). The mixture was cooled to 0° C. and 1-chloropropan-2-one (0.90 g, 9.78 mmol) in solution in DMF (5 mL) was added. Stirring was continued for 2 hours at 40° C. The mixture was filtered, and concentrated under vacuo. Column chromatography (0% to 7% 2N $NH_3$/MeOH in $CH_2Cl_2$) gave the title compound (0.32 g, 27%) as a light orange solid. MS (ES+) m/z 297.2 [M+H].

Step 2: tert-butyl N-[4-[acetonyl(formyl)amino]-1-bicyclo[2.2.2]octanyl]carbamate Acetic anhydride (0.42 g, 0.39 mL, 4.1 mmol) was added to formic acid (0.74 g, 0.63 mL, 16.2 mmol) and stirred for 1 hour. A solution of tert-butyl N-[4-(acetonylamino)-1-bicyclo[2.2.2]octanyl]carbamate (0.32 g, 1.08 mmol) in THF (8 mL) was added. The resulting dark solution was stirred for 30 minutes and then poured into $H_2O$ (30 mL). EtOAc (50 mL) was added and the biphase mixture was stirred and the pH adjusted to 8-9 by addition of $NaHCO_3$ in small portions. The organic phase was then separated, dried over $Na_2SO_4$ and concentrated under vacuo. A column chromatography (30% to 100% EtOAc in Heptane) gave the title compound (0.29 g, 82%) as a brown foam. MS (ES+) m/z 325.2 [M+H].

Step 3: tert-butyl N-[4-(4-methylimidazol-1-yl)-1-bicyclo[2.2.2]octanyl]carbamate To a solution of tert-butyl N-[4-[acetonyl(formyl)amino]-1-bicyclo[2.2.2]octanyl]carbamate (0.29 g, 0.89 mmol) in acetic acid (4 mL) was added ammonium acetate (0.34 g, 4.47 mmol). The reaction mixture was heated at 100° C. overnight and a second portion of ammonium acetate (0.14 g, 1.82 mmol) was added and stirring continued for an other 14 hours. The volatiles were removed under vacuo, and a column chromatography (0% to 10% 2N $NH_3$/MeOH in TBME) gave the title product (0.072 g, 26%) as an off-white solid. MS (ES+) m/z 306.2 [M+H].

Step 4: 4-(4-methylimidazol-1-yl)bicyclo[2.2.2]octan-1-amine. hydrochloride

To a suspension of tert-butyl N-[4-(4-methylimidazol-1-yl)-1-bicyclo[2.2.2]octanyl]carbamate (0.072 g, 0.237 mmol) in acetone (4 mL) was added aqueous HCl (0.20 mL, 2.13 mmol) resulting in a pale yellow solution. The mixture was stirred an additional 5 hours and the solid was collected and dried under vacuo to give the title product (0.054 g, 95%) as a white solid. MS (ES+) m/z 206.2 [M+H].

Intermediates of Type 12

Intermediate 12-1

6-chloro-2-(2,3,4-trifluorophenyl)hexanoic acid

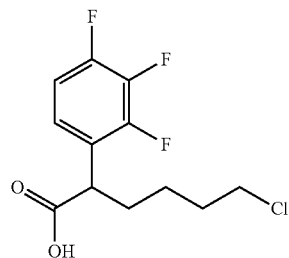 [SMILES: O=C(O)C(CCCCCl)c1ccc(F)c(F)c1F]

To a solution of 2-(2,3,4-trifluorophenyl)acetic acid (2 mmol) in toluene (3 mL) at −45° C. was added NaHMDS 1M in THF (4.2 mmol). The reaction was stirred at this temperature for 1 hour before being cannulated into a solution of 1-chloro-4-iodobutane (2.2 mmol) in toluene also at −45° C. The resulting reaction mixture was then warmed to RT slowly over one hour and stirred an other 30 minutes. HCl 2M was added until pH=1, and the product was extracted with EtOAc. The organic phase was dried over $Na_2SO_4$, filtered and concentrated under vacuo. Column chromatography ($SiO_2$, $CH_2Cl_2$/MeOH) afforded the title product (29%) as a colorless oil. MS (ES+) m/z: 279.2 [(M−H)+].

Intermediate 12-2

6-chloro-2-(3-chlorophenyl)hexanoic Acid

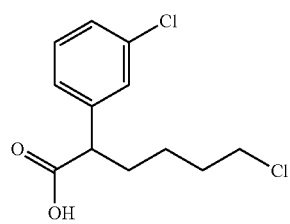 [SMILES: O=C(O)C(CCCCCl)c1cccc(Cl)c1]

With a similar method as for the preparation of intermediate 12-1, from 2-(3-chlorophenyl)acetic acid was prepared the title compound as a solid. MS (ES+) m/z: 259.3 [(M−H)+].

Intermediate 12-3

6-chloro-2-(4-chlorophenyl)hexanoic Acid

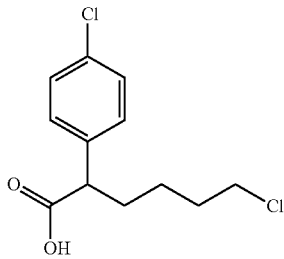 [SMILES: O=C(O)C(CCCCCl)c1ccc(Cl)cc1]

With a similar method as for the preparation of intermediate 12-1, from 2-(4-chlorophenyl)acetic acid was prepared the title compound as a solid. MS (ES+) m/z: 259.2 [(M−H)+].

Intermediate 12-4

6-chloro-2-(4-fluorophenyl)hexanoic Acid

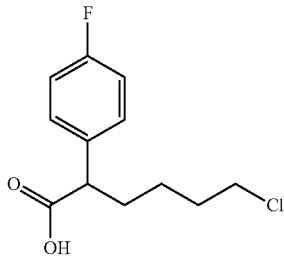 [SMILES: O=C(O)C(CCCCCl)c1ccc(F)cc1]

With a similar method as for the preparation of intermediate 12-1, from 2-(4-fluorophenyl)acetic acid was prepared the title compound as a light yellow oil. MS (ES+) m/z: 243.1 [(M−H)+].

Intermediate 12-5

6-chloro-2-(3,4-difluorophenyl)hexanoic Acid

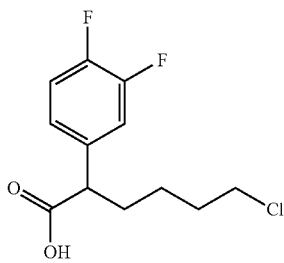 [SMILES: O=C(O)C(CCCCCl)c1ccc(F)c(F)c1]

With a similar method as for the preparation of intermediate 12-1, from 2-(3,4-difluorophenyl)acetic acid was prepared the title compound as a light yellow oil. MS (ES+) m/z: 261.3 [(M−H)+].

Intermediate 12-6

6-chloro-2-(3-chloro-5-fluoro-phenyl)hexanoic Acid

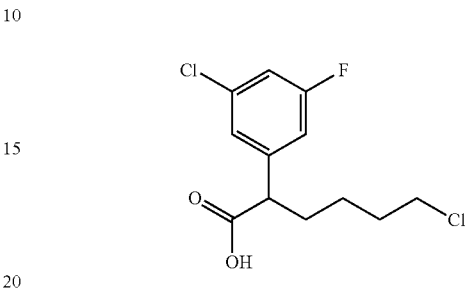

With a similar method as for the preparation of intermediate 12-1, from 2-(3-chloro-5-fluoro-phenyl)acetic acid was prepared the title compound as a light yellow oil. MS (ES+) m/z: 277.3 [(M−H)+].

Intermediate 12-7

6-chloro-2-(2-fluorophenyl)hexanoic acid

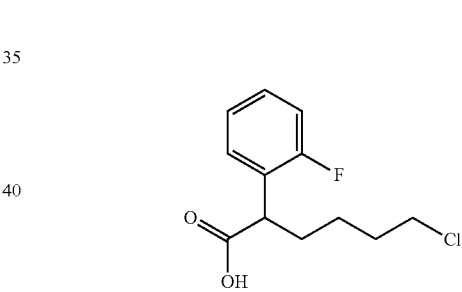

With a similar method as for the preparation of intermediate 12-1, from 2-(2-fluorophenyl)acetic acid was prepared the title compound as a light yellow oil. MS (ES+) m/z: 243.2 [(M−H)+].

General Procedure: Buchwald Coupling Reaction

To a solution of an intermediate 7, in 1,4-dioxane was added 1.1 equivalent of an intermediate 8. The reaction mixture was degased and a palladium catalyst [either dibromo-bis-(tritert.-butyl)-phosphine-palladium (0.1 eq. CAS185812-86-6) or tri(dibenzylidenacetonne) dipalladium (0) CAS51364-51-3 in the presence of 2-di-tert-butylphosphino-2',4',6'-triisopropylbiphenyl CAS564483-19-8] and NaOtBu (2.1 eq.) were added. The reaction mixture was heated at 100° C. until completion of the reaction (usually between 2 and 8 hours) and concentrated under vacuo. A purification was done either by column chromatography or reverse phase preparative HPLC to afford the desired product.

Example 1 and 2

(9R)-9-(3-chlorophenyl)-N-[3-(4-methylimidazol-1-yl)-1-bicyclo[1.1.1]pentanyl]-6,7,8,9-tetrahydro-5H-[1,2,4]triazolo[1,5-a]azepin-2-amine and (9S)-9-(3-chlorophenyl)-N-[3-(4-methylimidazol-1-yl)-1-bicyclo[1.1.1]pentanyl]-6,7,8,9-tetrahydro-5H-[1,2,4]triazolo[1,5-a]azepin-2-amine

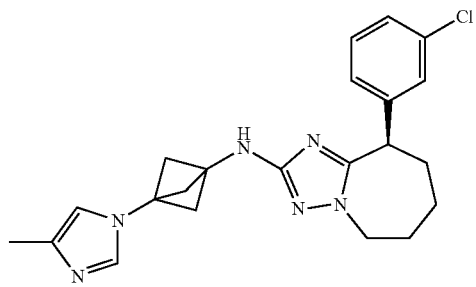

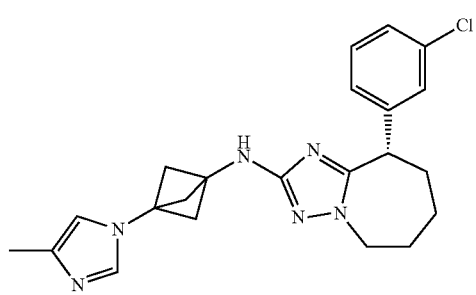

Step 1: 1-(3-isothiocyanato-1-bicyclo[1.1.1]pentanyl)-4-methyl-imidazole

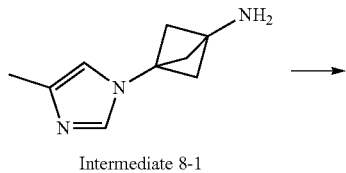

Intermediate 8-1

To a solution of 3-(4-methylimidazol-1-yl)bicyclo[1.1.1]pentan-1-amine (intermediate 8-1) (1.08 g, 6.62 mmol) in CH$_2$Cl$_2$ (30 mL) was added 1-(2-oxopyridine-1-carbothioyl)pyridin-2-one (1.74 g, 7.28 mmol) and NEt(iPr)$_2$ (1.16 mL, 6.62 mmol). The reaction mixture was stirred at RT over night, concentrated under vacuo and the crude residue was used directly in the next step without further purification.

Step 2: [3-(4-methylimidazol-1-yl)-1-bicyclo[1.1.1]pentanyl]thiourea

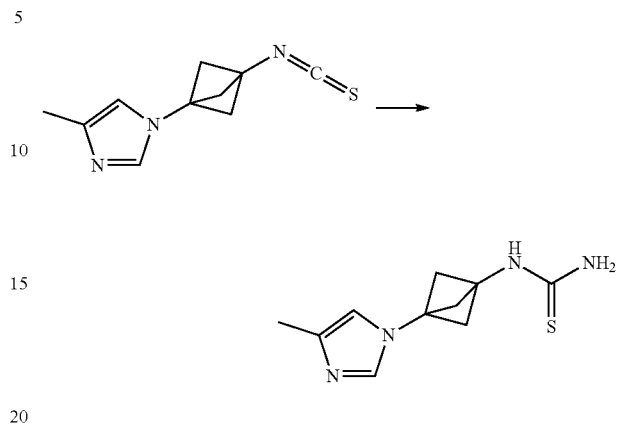

To a solution of ammonia 7N in MeOH (20.3 mL, 142 mmol) was added 1-(3-isothiocyanato-1-bicyclo[1.1.1]pentanyl)-4-methyl-imidazole (crude product from step 1) in solution in MeOH (5 mL). The reaction mixture was stirred at RT for two hours. The reaction mixture was concentrated under vacuo and the residue purified by column chromatography (2M NH3/MeOH in CH$_2$Cl$_2$; gradient: 2.5-10%) to afford 1.22 g (81% over two steps) of [3-(4-methylimidazol-1-yl)-1-bicyclo[1.1.1]pentanyl]thiourea as a very light brown solid. MS (ES+) m/z: 223.2 [(M+H)$^+$].

Step 3: 2-methyl-3-[3-(4-methylimidazol-1-yl)-1-bicyclo[1.1.1]pentanyl]isothiourea hydroiodide

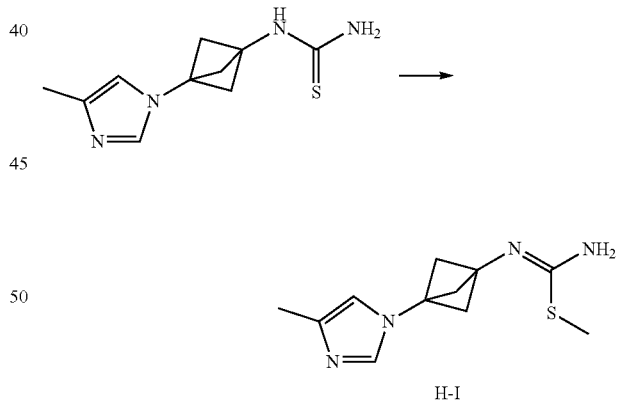

In a sealed tube, to a solution of [3-(4-methylimidazol-1-yl)-1-bicyclo[1.1.1]pentanyl]thiourea (1.22 g, 5.49 mmol) in EtOH (15 mL) was added MeI (0.41 mL, 6.59 mmol). The reaction mixture was stirred for 48 hours. The reaction mixture was concentrated under vacuo and the resulting solid was triturated in Et$_2$O, the product collected by filtration and dried under vacuo to afford 2.0 g (98%) of 2-methyl-3-[3-(4-methylimidazol-1-yl)-1-bicyclo[1.1.1]pentanyl]isothiourea hydroiodide as a white solid. MS (ES+) m/z: 237.2 [(M+H)$^+$].

Step 4: 6-chloro-2-(3-chlorophenyl)-N-[(Z)-N-[3-(4-methylimidazol-1-yl)-1-bicyclo[1.1.1]pentanyl]-C-methylsulfanyl-carbonimidoyl]hexanamide

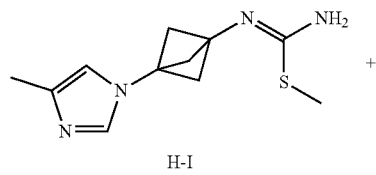

H-I

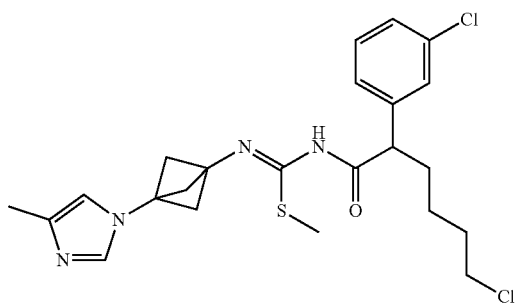

Intermediate 12-2

To a solution of 2-methyl-3-[3-(4-methylimidazol-1-yl)-1-bicyclo[1.1.1]pentanyl]isothiourea hydroiodide (453 mg, 1.24 mmol) in DMF (15 mL) was added 6-chloro-2-(3-chlorophenyl) hexanoic acid (intermediate 12-2, 325 mg, 1.24 mmol), HOBt (572 mg, 3.73 mmol), EDC.HCl (716 mg, 3.73 mmol) and NEt(iPr)$_2$ (1.74 mL, 9.96 mmol). The reaction mixture was stirred at RT for five hours and then poured into water. The product was extracted with EtOAc three times, and the combined organic phase was dried over Na$_2$SO$_4$, and concentrated under vacuo. The crude product 6-chloro-2-(3-chlorophenyl)-N-[(Z)-N-[3-(4-methylimidazol-1-yl)-1-bicyclo[1.1.1]pentanyl]-C-methylsulfanyl-carbonimidoyl]hexanamide (light yellow viscous oil) was used directly in the next step without further purification.

Step 5: 5-[5-chloro-1-(3-chlorophenyl)pentyl]-N-[3-(4-methylimidazol-1-yl)-1-bicyclo[1.1.1]pentanyl]-4H-1,2,4-triazol-3-amine

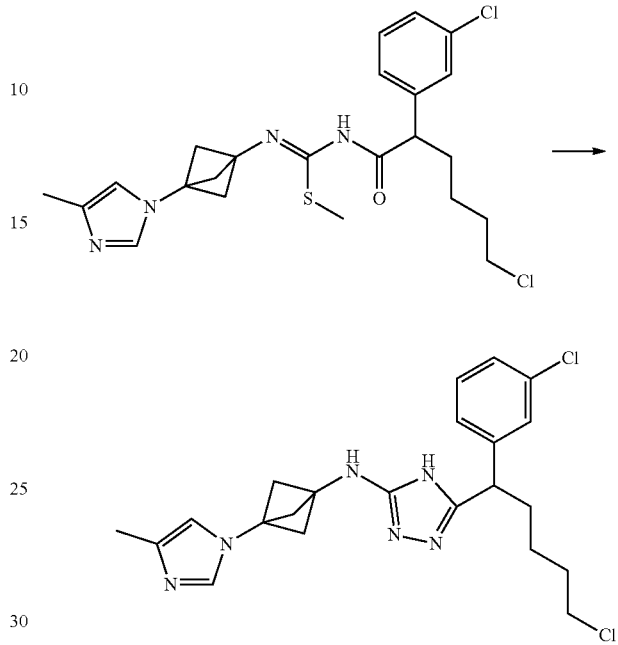

To a solution of 6-chloro-2-(3-chlorophenyl)-N-[(Z)-N-[3-(4-methylimidazol-1-yl)-1-bicyclo[1.1.1]pentanyl]-C-methylsulfanyl-carbonimidoyl]hexanamide (crude product from step 4) in THF (15 mL) was added hydrazine monohydrate (312 mg, 6.2 mmol). The reaction mixture was stirred at reflux for four hours and concentrated under vacuo. The residue was taken up in EtOAc and washed with water. The organic phase was dried over Na$_2$SO$_4$, concentrated and dried under vacuo to afford 5-[5-chloro-1-(3-chlorophenyl)pentyl]-N-[3-(4-methylimidazol-1-yl)-1-bicyclo[1.1.1]pentanyl]-4H-1,2,4-triazol-3-amine as a yellow viscous oil. The crude was used directly in the next last step without further purification.

Step 6: 9-(3-chlorophenyl)-N-[3-(4-methylimidazol-1-yl)-1-bicyclo[1.1.1]pentanyl]-6,7,8,9-tetrahydro-5H-[1,2,4]triazolo[1,5-a]azepin-2-amine

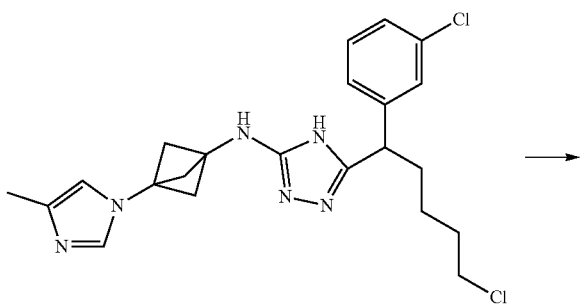

-continued

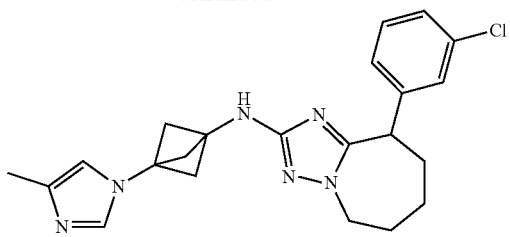

To a solution of 5-[5-chloro-1-(3-chlorophenyl)pentyl]-N-[3-(4-methylimidazol-1-yl)-1-bicyclo[1.1.1]pentanyl]-4H-1,2,4-triazol-3-amine (crude product from step 5) in DMF (15 mL) was added K₂CO₃ (516 mg, 3.73 mmol) and KI (310 mg, 1.87 mmol). The reaction mixture was heated at 85° C. for 4 hours and concentrated under vacuo. A column chromatography (SiO₂, CH₂Cl₂/MeOH) gave 96 mg (18% over the last three steps) of 9-(3-chlorophenyl)-N-[3-(4-methylimidazol-1-yl)-1-bicyclo[1.1.1]pentanyl]-6,7,8,9-tetrahydro-5H-[1,2,4]triazolo[1,5-a]azepin-2-amine as a white solid. MS (ES+) m/z: 409.3 [(M+H)⁺].

Step 7: (9R)-9-(3-chlorophenyl)-N-[3-(4-methylimidazol-1-yl)-1-bicyclo[1.1.1]pentanyl]-6,7,8,9-tetrahydro-5H-[1,2,4]triazolo[1,5-a]azepin-2-amine and (9S)-9-(3-chlorophenyl)-N-[3-(4-methylimidazol-1-yl)-1-bicyclo[1.1.1]pentanyl]-6,7,8,9-tetrahydro-5H-[1,2,4]triazolo[1,5-a]azepin-2-amine

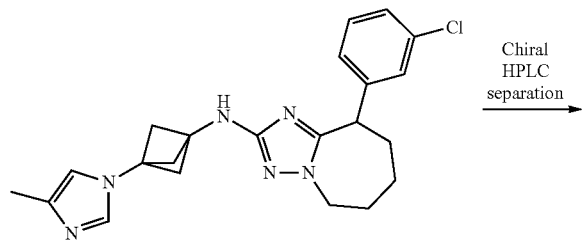

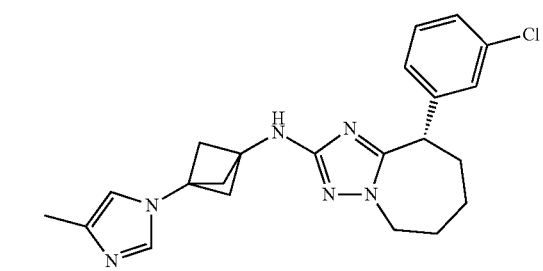

90 mg (0.22 mmol) of the racemic 9-(3-chlorophenyl)-N-[3-(4-methylimidazol-1-yl)-1-bicyclo[1.1.1]pentanyl]-6,7,8,9-tetrahydro-5H-[1,2,4]triazolo[1,5-a]azepin-2-amine was used for chiral HPLC resolution providing 30 mg of (9R)-9-(3-chlorophenyl)-N-[3-(4-methylimidazol-1-yl)-1-bicyclo[1.1.1]pentanyl]-6,7,8,9-tetrahydro-5H-[1,2,4]triazolo[1,5-a]azepin-2-amine as a white solid (MS (ES+) m/z: 409.3 [(M+H)⁺]) and 31 mg of (9S)-9-(3-chlorophenyl)-N-[3-(4-methylimidazol-1-yl)-1-bicyclo[1.1.1]pentanyl]-6,7,8,9-tetrahydro-5H-[1,2,4]triazolo[1,5-a]azepin-2-amine as a white solid; MS (ES+) m/z: 409.3 [(M+H)⁺].

Example 3 and 4

(9R)-9-(4-fluorophenyl)-N-[3-(4-methylimidazol-1-yl)-1-bicyclo[1.1.1]pentanyl]-6,7,8,9-tetrahydro-5H-[1,2,4]triazolo[1,5-a]azepin-2-amine and (9S)-9-(4-fluorophenyl)-N-[3-(4-methylimidazol-1-yl)-1-bicyclo[1.1.1]pentanyl]-6,7,8,9-tetrahydro-5H-[1,2,4]triazolo[1,5-a]azepin-2-amine

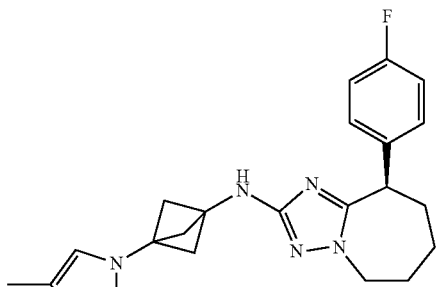

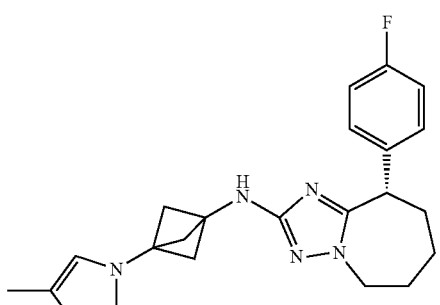

In analogy to the preparation of compounds described example 1 and 2, using the intermediate 12-4 in the step 4, was prepared 29 mg of (9R)-9-(4-fluorophenyl)-N-[3-(4-methylimidazol-1-yl)-1-bicyclo[1.1.1]pentanyl]-6,7,8,9-tetrahydro-5H-[1,2,4]triazolo[1,5-a]azepin-2-amine as a white solid (MS (ES+) m/z: 393.3 [(M+H)⁺]) and 29 mg of (9S)-9-(4-fluorophenyl)-N-[3-(4-methylimidazol-1-yl)-1-bicyclo[1.1.1]pentanyl]-6,7,8,9-tetrahydro-5H-[1,2,4]triazolo[1,5-a]azepin-2-amine as a white solid; MS (ES+) m/z: 393.3 [(M+H)⁺].

Example 5 and 6

(9R)-9-(4-chlorophenyl)-N-[3-(4-methylimidazol-1-yl)-1-bicyclo[1.1.1]pentanyl]-6,7,8,9-tetrahydro-5H-[1,2,4]triazolo[1,5-a]azepin-2-amine and (9S)-9-(4-chlorophenyl)-N-[3-(4-methylimidazol-1-yl)-1-bicyclo[1.1.1]pentanyl]-6,7,8,9-tetrahydro-5H-[1,2,4]triazolo[1,5-a]azepin-2-amine

Example 7 and 8

(9R)-9-(3-chloro-5-fluoro-phenyl)-N-[4-(4-methylimidazol-1-yl)-1-bicyclo[2.2.2]octanyl]-6,7,8,9-tetrahydro-5H-[1,2,4]triazolo[1,5-a]azepin-2-amine and (9S)-9-(3-chloro-5-fluoro-phenyl)-N-[4-(4-methylimidazol-1-yl)-1-bicyclo[2.2.2]octanyl]-6,7,8,9-tetrahydro-5H-[1,2,4]triazolo[1,5-a]azepin-2-amine

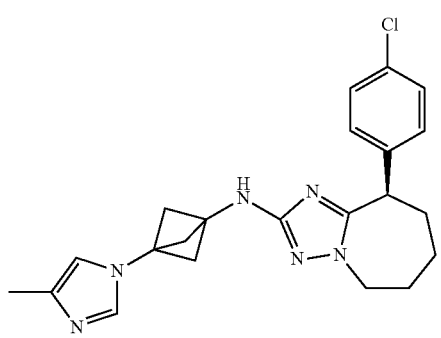

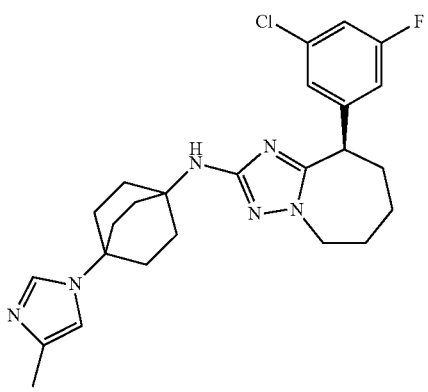

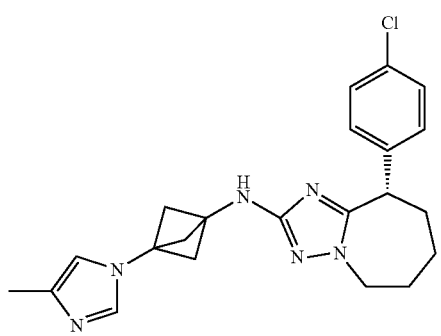

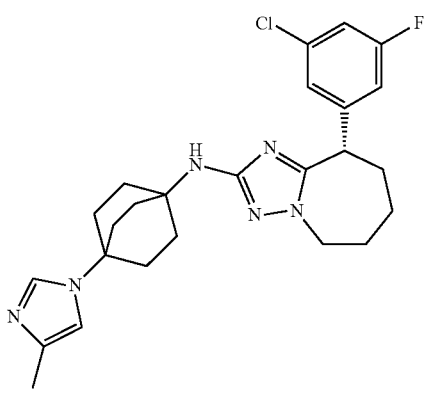

In analogy to the preparation of compounds described example 1 and 2, using the intermediate 12-3 in the step 4, was prepared 35 mg of (9R)-9-(4-chlorophenyl)-N-[3-(4-methylimidazol-1-yl)-1-bicyclo[1.1.1]pentanyl]-6,7,8,9-tetrahydro-5H-[1,2,4]triazolo[1,5-a]azepin-2-amine as a white solid (MS (ES+) m/z: 409.3 [(M+H)$^+$]) and 34 mg of (9S)-9-(4-chlorophenyl)-N-[3-(4-methylimidazol-1-yl)-1-bicyclo[1.1.1]pentanyl]-6,7,8,9-tetrahydro-5H-[1,2,4]triazolo[1,5-a]azepin-2-amine as a white solid; MS (ES+) m/z: 409.3 [(M+H)$^+$].

Using the general procedure of the Buchwald coupling between the intermediate (7.2) 2-bromo-9-(3-chloro-5-fluoro-phenyl)-6,7,8,9-tetrahydro-5H-[1,2,4]triazolo[1,5-a]azepine and the intermediate (8-2) 4-(4-methylimidazol-1-yl)bicyclo[2.2.2]octan-1-amine hydrochloride following a chiral HPLC separation of the enantiomeres was prepared 13 mg of (9R)-9-(3-chloro-5-fluoro-phenyl)-N-[4-(4-methylimidazol-1-yl)-1-bicyclo[2.2.2]octanyl]-6,7,8,9-tetrahydro-5H-[1,2,4]triazolo[1,5-a]azepin-2-amine as a white solid (MS (ES+) m/z: 469.4 [(M+H)$^+$]) and 13 mg of (9S)-9-(3-chloro-5-fluoro-phenyl)-N-[4-(4-methylimidazol-1-yl)-1-bicyclo[2.2.2]octanyl]-6,7,8,9-tetrahydro-5H-[1,2,4]triazolo[1,5-a]azepin-2-amine as a white solid (MS (ES+) m/z: 469.4 [(M+H)$^+$]).

Example 9 and 10

(9R)-9-(3-chloro-5-fluoro-phenyl)-N-[3-(4-methyl-imidazol-1-yl)-1-bicyclo[1.1.1]pentanyl]-6,7,8,9-tetrahydro-5H-[1,2,4]triazolo[1,5-a]azepin-2-amine and (9S)-9-(3-chloro-5-fluoro-phenyl)-N-[3-(4-methylimidazol-1-yl)-1-bicyclo[1.1.1]pentanyl]-6,7,8,9-tetrahydro-5H-[1,2,4]triazolo[1,5-a]azepin-2-amine

Example 11 and 12

(9R)-9-(3,4-difluorophenyl)-N-[4-(4-methylimidazol-1-yl)-1-bicyclo[2.2.2]octanyl]-6,7,8,9-tetrahydro-5H-[1,2,4]triazolo[1,5-a]azepin-2-amine and (9S)-9-(3,4-difluorophenyl)-N-[4-(4-methylimidazol-1-yl)-1-bicyclo[2.2.2]octanyl]-6,7,8,9-tetrahydro-5H-[1,2,4]triazolo[1,5-a]azepin-2-amine

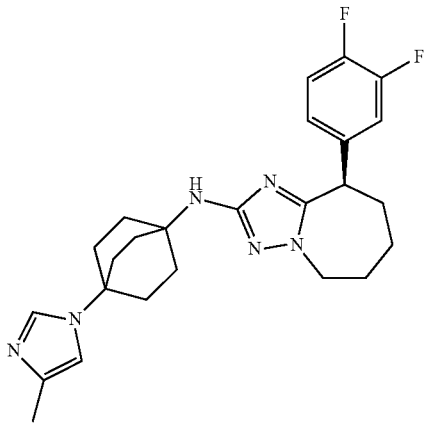

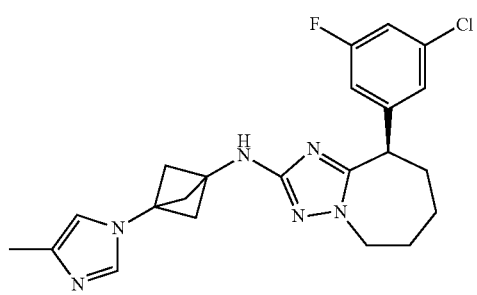

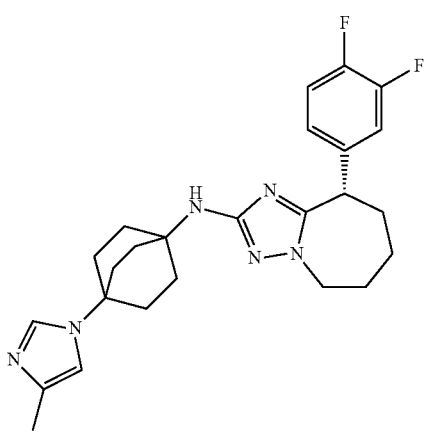

In analogy to the preparation of compounds described example 1 and 2, using the intermediate 12-6 in the step 4, was prepared 20 mg of (9R)-9-(3-chloro-5-fluoro-phenyl)-N-[3-(4-methylimidazol-1-yl)-1-bicyclo[1.1.1]pentanyl]-6,7,8,9-tetrahydro-5H-[1,2,4]triazolo[1,5-a]azepin-2-amine as a white solid (MS (ES+) m/z: 427.3 [(M+H)$^+$]) and 20 mg of (9S)-9-(3-chloro-5-fluoro-phenyl)-N-[3-(4-methylimidazol-1-yl)-1-bicyclo[0.1.1.1]pentanyl]-6,7,8,9-tetrahydro-5H-[1,2,4]triazolo[1,5-a]azepin-2-amine as a white solid; MS (ES+) m/z: 427.3 [(M+H)$^+$].

Using the general procedure of the Buchwald coupling between the intermediate (7.3) 2-bromo-9-(3,4-difluorophenyl)-6,7,8,9-tetrahydro-5H-[1,2,4]triazolo[1,5-a]azepine and the intermediate (8-2) 4-(4-methylimidazol-1-yl)bicyclo[2.2.2]octan-1-amine hydrochloride following a chiral HPLC separation of the enantiomers was prepared 63 mg of (9R)-9-(3,4-difluorophenyl)-N-[4-(4-methylimidazol-1-yl)-1-bicyclo[2.2.2]octanyl]-6,7,8,9-tetrahydro-5H-[1,2,4]triazolo[1,5-a]azepin-2-amine as a white solid (MS (ES+) m/z: 453.4 [(M+H)$^+$]) and 63 mg of (9S)-9-(3,4-difluorophenyl)-N-[4-(4-methylimidazol-1-yl)-1-bicyclo[2.2.2]octanyl]-6,7,8,9-tetrahydro-5H-[1,2,4]triazolo[1,5-a]azepin-2-amine as a white solid (MS (ES+) m/z: 453.4 [(M+H)$^+$]).

Example 13 and 14

(9R)-9-(3,4-difluorophenyl)-N-[3-(4-methylimidazol-1-yl)-1-bicyclo[1.1.1]pentanyl]-6,7,8,9-tetrahydro-5H-[1,2,4]triazolo[1,5-a]azepin-2-amine and (9S)-9-(3,4-difluorophenyl)-N-[3-(4-methylimidazol-1-yl)-1-bicyclo[1.1.1]pentanyl]-6,7,8,9-tetrahydro-5H-[1,2,4]triazolo[1,5-a]azepin-2-amine

Example 15 and 16

(9R)-9-(2-fluorophenyl)-N-[3-(4-methylimidazol-1-yl)-1-bicyclo[1.1.1]pentanyl]-6,7,8,9-tetrahydro-5H-[1,2,4]triazolo[1,5-a]azepin-2-amine and (9S)-9-(2-fluorophenyl)-N-[3-(4-methylimidazol-1-yl)-1-bicyclo[1.1.1]pentanyl]-6,7,8,9-tetrahydro-5H-[1,2,4]triazolo[1,5-a]azepin-2-amine

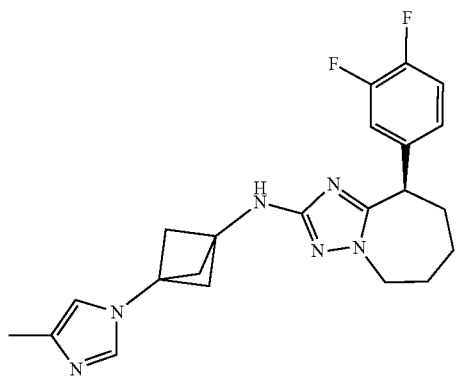

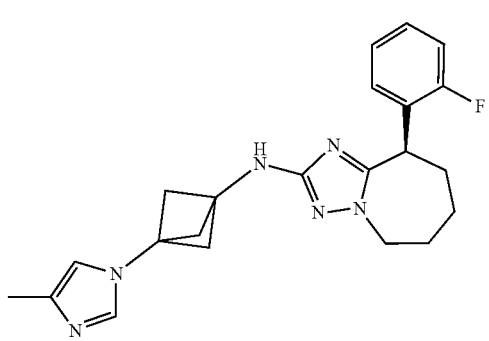

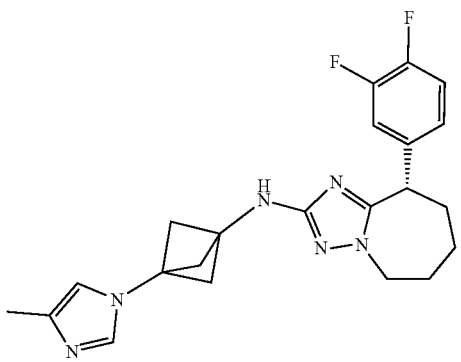

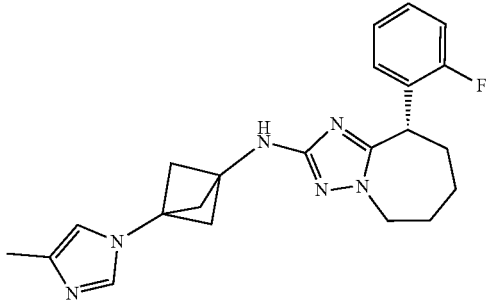

In analogy to the preparation of compounds described example 1 and 2, using the intermediate 12-5 in the step 4, was prepared 11 mg of (9R)-9-(3,4-difluorophenyl)-N-[3-(4-methylimidazol-1-yl)-1-bicyclo[1.1.1]pentanyl]-6,7,8,9-tetrahydro-5H-[1,2,4]triazolo[1,5-a]azepin-2-amine as a white solid (MS (ES+) m/z: 411.3 [(M+H)$^+$]) and 11 mg of (9S)-9-(3,4-difluorophenyl)-N-[3-(4-methylimidazol-1-yl)-1-bicyclo[1.1.1]pentanyl]-6,7,8,9-tetrahydro-5H-[1,2,4]triazolo[1,5-a]azepin-2-amine as a white solid; MS (ES+) m/z: 411.3 [(M+H)$^+$].

In analogy to the preparation of compounds described example 1 and 2, using the intermediate 12-7 in the step 4, was prepared 15 mg of (9R)-9-(2-fluorophenyl)-N-[3-(4-methylimidazol-1-yl)-1-bicyclo[1.1.1]pentanyl]-6,7,8,9-tetrahydro-5H-[1,2,4]triazolo[1,5-a]azepin-2-amine as a white solid (MS (ES+) m/z: 393.2 [(M+H)$^+$]) and 15 mg of (9S)-9-(2-fluorophenyl)-N-[3-(4-methylimidazol-1-yl)-1-bicyclo[1.1.1]pentanyl]-6,7,8,9-tetrahydro-5H-[1,2,4]triazolo[1,5-a]azepin-2-amine as a white solid; MS (ES+) m/z: 393.2 [(M+H)$^+$].

Example 17 and 18

(9R)-9-(2-fluorophenyl)-N-[4-(4-methylimidazol-1-yl)-1-bicyclo[2.2.2]octanyl]-6,7,8,9-tetrahydro-5H-[1,2,4]triazolo[1,5-a]azepin-2-amine and (9S)-9-(2-fluorophenyl)-N-[4-(4-methylimidazol-1-yl)-1-bicyclo[2.2.2]octanyl]-6,7,8,9-tetrahydro-5H-[1,2,4]triazolo[1,5-a]azepin-2-amine

Example 19 and 20

(9R)-N-[3-(4-methylimidazol-1-yl)-1-bicyclo[1.1.1]pentanyl]-9-(2,3,4-trifluorophenyl)-6,7,8,9-tetrahydro-5H-[1,2,4]triazolo[1,5-a]azepin-2-amine and (9S)-N-[3-(4-methylimidazol-1-yl)-1-bicyclo[1.1.1]pentanyl]-9-(2,3,4-trifluorophenyl)-6,7,8,9-tetrahydro-5H-[1,2,4]triazolo[1,5-a]azepin-2-amine

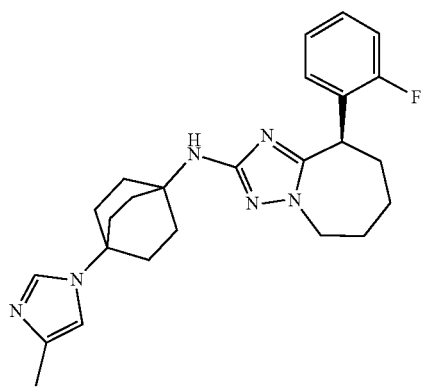

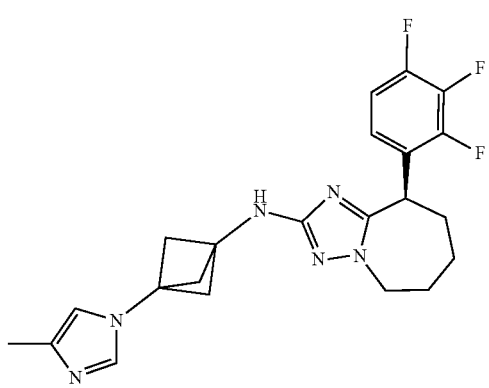

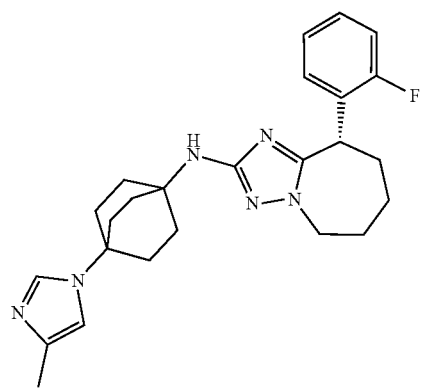

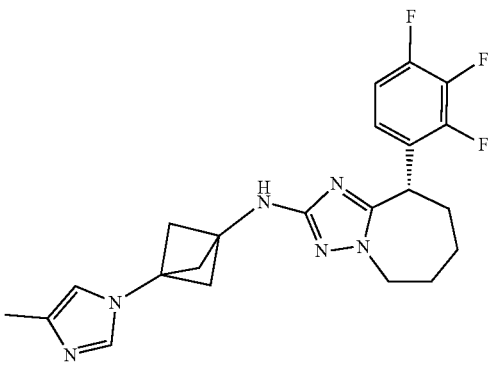

Using the general procedure of the Buchwald coupling between the intermediate (7.4) 2-bromo-9-(2-fluorophenyl)-6,7,8,9-tetrahydro-5H-[1,2,4]triazolo[1,5-a]azepine and the intermediate (8-2) 4-(4-methylimidazol-1-yl)bicyclo[2.2.2]octan-1-amine hydrochloride following a chiral HPLC separation of the enantiomers was prepared 19 mg of (9R)-9-(2-fluorophenyl)-N-[4-(4-methylimidazol-1-yl)-1-bicyclo[2.2.2]octanyl]-6,7,8,9-tetrahydro-5H-[1,2,4]triazolo[1,5-a]azepin-2-amine as a white solid (MS (ES+) m/z: 435.4 [(M+H)$^+$]) and 19 mg of (9S)-9-(2-fluorophenyl)-N-[4-(4-methylimidazol-1-yl)-1-bicyclo[2.2.2]octanyl]-6,7,8,9-tetrahydro-5H-[1,2,4]triazolo[1,5-a]azepin-2-amine as a white solid (MS (ES+) m/z: 435.4 [(M+H)$^+$]).

In analogy to the preparation of compounds described example 1 and 2, using the intermediate 12-1 in the step 4, was prepared 19 mg of (9R)-N-[3-(4-methylimidazol-1-yl)-1-bicyclo[1.1.1]pentanyl]-9-(2,3,4-trifluorophenyl)-6,7,8,9-tetrahydro-5H-[1,2,4]triazolo[1,5-a]azepin-2-amine as a white solid (MS (ES+) m/z: 429.2 [(M+H)$^+$]) and 19 mg of (9S)-N-[3-(4-methylimidazol-1-yl)-1-bicyclo[1.1.1]pentanyl]-9-(2,3,4-trifluorophenyl)-6,7,8,9-tetrahydro-5H-[1,2,4]triazolo[1,5-a]azepin-2-amine as a white solid; MS (ES+) m/z: 429.2 [(M+H)$^+$].

Example 21 and 22

(9R)-N-[4-(4-methylimidazol-1-yl)-1-bicyclo[2.2.2]
octanyl]-9-(2,3,4-trifluorophenyl)-6,7,8,9-tetra-
hydro-5H-[1,2,4]triazolo[1,5-a]azepin-2-amine and
(9S)-N-[4-(4-methylimidazol-1-yl)-1-bicyclo[2.2.2]
octanyl]-9-(2,3,4-trifluorophenyl)-6,7,8,9-tetra-
hydro-5H-[1,2,4]triazolo[1,5-a]azepin-2-amine

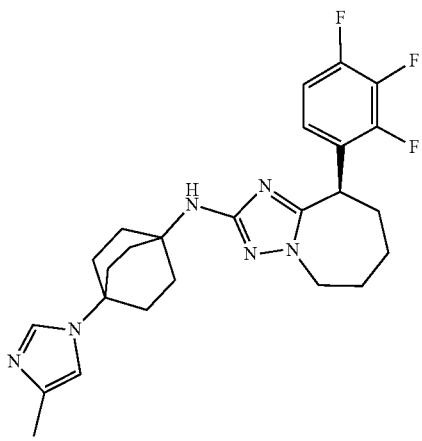

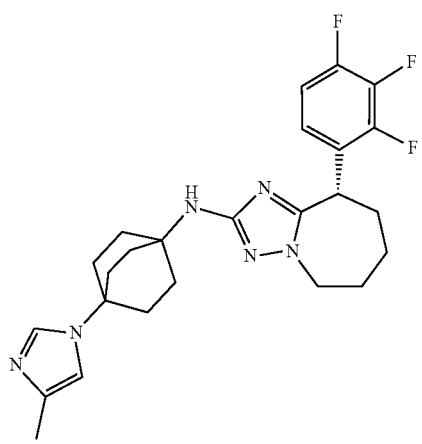

Using the general procedure of the Buchwald coupling between the intermediate (7.1) 2-bromo-9-(2,3,4-trifluorophenyl)-6,7,8,9-tetrahydro-5H-[1,2,4]triazolo[1,5-a]azepine and the intermediate (8-2) 4-(4-methylimidazol-1-yl)bicyclo[2.2.2]octan-1-amine hydrochloride following a chiral HPLC separation of the enantiomers was prepared 35 mg of (9R)-N-[4-(4-methylimidazol-1-yl)-1-bicyclo[2.2.2]octa-nyl]-9-(2,3,4-trifluorophenyl)-6,7,8,9-tetrahydro-5H-[1,2,4]triazolo[1,5-a]azepin-2-amine as a white solid (MS (ES+) m/z: 471.5 [(M+H)$^+$]) and 35 mg of (9S)-N-[4-(4-methyl-imidazol-1-yl)-1-bicyclo[2.2.2]octanyl]-9-(2,3,4-trifluoro-phenyl)-6,7,8,9-tetrahydro-5H-[1,2,4]triazolo[1,5-a]azepin-2-amine as a white solid (MS (ES+) m/z: 471.5 [(M+H)$^+$]).

The invention claimed is:

1. A compound of formula I

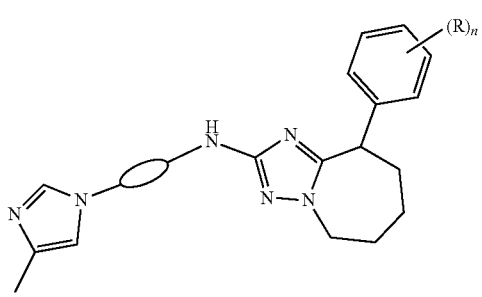

wherein:

R is hydrogen or halogen, wherein R may be different if n=2 or 3;

n is 1, 2 or 3; and

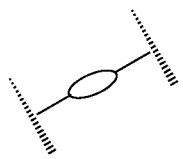

is a disubstituted bicyclo[1,1,1]pentane or bicyclo[2,2,2]octane selected from:

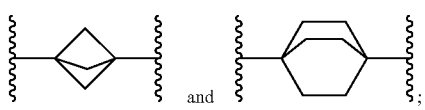

or a pharmaceutically acceptable acid addition salt thereof, or a racemic mixture or its corresponding enantiomer, or stereoisomer thereof.

2. A compound according to claim 1, wherein

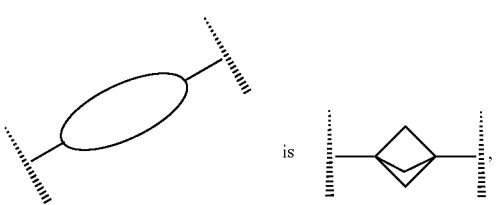

or a pharmaceutically acceptable acid addition salt thereof, or a racemic mixture or its corresponding enantiomer, or stereoisomer thereof.

3. A compound of claim 1, wherein

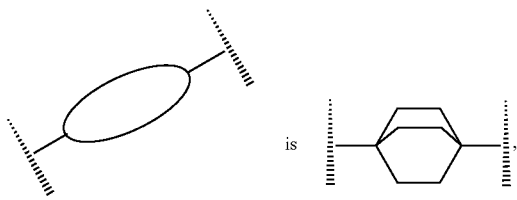

is or a pharmaceutically acceptable acid addition salt thereof, or a racemic mixture or its corresponding enantiomer, or stereoisomer thereof.

4. A compound of claim 2, selected from the group consisting of:
- (9R)-9-(3-chlorophenyl)-N-[3-(4-methylimidazol-1-yl)-1-bicyclo[1.1.1]pentanyl]-6,7,8,9-tetrahydro-5H-[1,2,4]triazolo[1,5-a]azepin-2-amine,
- (9S)-9-(3-chlorophenyl)-N-[3-(4-methylimidazol-1-yl)-1-bicyclo[1.1.1]pentanyl]-6,7,8,9-tetrahydro-5H-[1,2,4]triazolo[1,5-a]azepin-2-amine,
- (9R)-9-(4-fluorophenyl)-N-[3-(4-methylimidazol-1-yl)-1-bicyclo[1.1.1]pentanyl]-6,7,8,9-tetrahydro-5H-[1,2,4]triazolo[1,5-a]azepin-2-amine,
- (9S)-9-(4-fluorophenyl)-N-[3-(4-methylimidazol-1-yl)-1-bicyclo[1.1.1]pentanyl]-6,7,8,9-tetrahydro-5H-[1,2,4]triazolo[1,5-a]azepin-2-amine,
- (9R)-9-(4-chlorophenyl)-N-[3-(4-methylimidazol-1-yl)-1-bicyclo[1.1.1]pentanyl]-6,7,8,9-tetrahydro-5H-[1,2,4]triazolo[1,5-a]azepin-2-amine,
- (9S)-9-(4-chlorophenyl)-N-[3-(4-methylimidazol-1-yl)-1-bicyclo[1.1.1]pentanyl]-6,7,8,9-tetrahydro-5H-[1,2,4]triazolo[1,5-a]azepin-2-amine,
- (9R)-9-(3-chloro-5-fluoro-phenyl)-N-[3-(4-methylimidazol-1-yl)-1-bicyclo[1.1.1]pentanyl]-6,7,8,9-tetrahydro-5H-[1,2,4]triazolo[1,5-a]azepin-2-amine,
- (9S)-9-(3-chloro-5-fluoro-phenyl)-N-[3-(4-methylimidazol-1-yl)-1-bicyclo[1.1.1]pentanyl]-6,7,8,9-tetrahydro-5H-[1,2,4]triazolo[1,5-a]azepin-2-amine,
- (9R)-9-(3,4-difluorophenyl)-N-[3-(4-methylimidazol-1-yl)-1-bicyclo[1.1.1]pentanyl]-6,7,8,9-tetrahydro-5H-[1,2,4]triazolo[1,5-a]azepin-2-amine,
- (9S)-9-(3,4-difluorophenyl)-N-[3-(4-methylimidazol-1-yl)-1-bicyclo[1.1.1]pentanyl]-6,7,8,9-tetrahydro-5H-[1,2,4]triazolo[1,5-a]azepin-2-amine,
- (9R)-9-(2-fluorophenyl)-N-[3-(4-methylimidazol-1-yl)-1-bicyclo[1.1.1]pentanyl]-6,7,8,9-tetrahydro-5H-[1,2,4]triazolo[1,5-a]azepin-2-amine,
- (9S)-9-(2-fluorophenyl)-N-[3-(4-methylimidazol-1-yl)-1-bicyclo[1.1.1]pentanyl]-6,7,8,9-tetrahydro-5H-[1,2,4]triazolo[1,5-a]azepin-2-amine,
- (9R)-N-[3-(4-methylimidazol-1-yl)-1-bicyclo[1.1.1]pentanyl]-9-(2,3,4-trifluorophenyl)-6,7,8,9-tetrahydro-5H-[1,2,4]triazolo[1,5-a]azepin-2-amine, or
- (9S)-N-[3-(4-methylimidazol-1-yl)-1-bicyclo[1.1.1]pentanyl]-9-(2,3,4-trifluorophenyl)-6,7,8,9-tetrahydro-5H-[1,2,4]triazolo[1,5-a]azepin-2-amine.

5. A compound of claim 3, selected from the group consisting of:
- (9R)-9-(3-chloro-5-fluoro-phenyl)-N-[4-(4-methylimidazol-1-yl)-1-bicyclo[2.2.2]octanyl]-6,7,8,9-tetrahydro-5H-[1,2,4]triazolo[1,5-a]azepin-2-amine,
- (9S)-9-(3-chloro-5-fluoro-phenyl)-N-[4-(4-methylimidazol-1-yl)-1-bicyclo[2.2.2]octanyl]-6,7,8,9-tetrahydro-5H-[1,2,4]triazolo[1,5-a]azepin-2-amine,
- (9R)-9-(3,4-difluorophenyl)-N-[4-(4-methylimidazol-1-yl)-1-bicyclo[2.2.2]octanyl]-6,7,8,9-tetrahydro-5H-[1,2,4]triazolo[1,5-a]azepin-2-amine,
- (9S)-9-(3,4-difluorophenyl)-N-[4-(4-methylimidazol-1-yl)-1-bicyclo[2.2.2]octanyl]-6,7,8,9-tetrahydro-5H-[1,2,4]triazolo[1,5-a]azepin-2-amine,
- (9R)-9-(2-fluorophenyl)-N-[4-(4-methylimidazol-1-yl)-1-bicyclo[2.2.2]octanyl]-6,7,8,9-tetrahydro-5H-[1,2,4]triazolo[1,5-a]azepin-2-amine,
- (9S)-9-(2-fluorophenyl)-N-[4-(4-methylimidazol-1-yl)-1-bicyclo[2.2.2]octanyl]-6,7,8,9-tetrahydro-5H-[1,2,4]triazolo[1,5-a]azepin-2-amine,
- (9R)-N-[4-(4-methylimidazol-1-yl)-1-bicyclo[2.2.2]octanyl]-9-(2,3,4-trifluorophenyl)-6,7,8,9-tetrahydro-5H-[1,2,4]triazolo[1,5-a]azepin-2-amine, or
- (9S)-N-[4-(4-methylimidazol-1-yl)-1-bicyclo[2.2.2]octanyl]-9-(2,3,4-trifluorophenyl)-6,7,8,9-tetrahydro-5H-[1,2,4]triazolo[1,5-a]azepin-2-amine.

6. A pharmaceutical preparation containing one or more compounds of claim 1 and pharmaceutically acceptable excipients.

7. A pharmaceutical preparation containing one or more compounds of claim 4 and pharmaceutically acceptable excipients.

8. A pharmaceutical preparation containing one or more compounds of claim 5 and pharmaceutically acceptable excipients.

9. A method of treating Alzheimer's disease, cerebral amyloid angiopathy, hereditary cerebral hemorrhage with amyloidosis, Dutch-type (HCHWA-D), multi-infarct dementia, dementia pugilistica or Down syndrome, which method comprises administering to an adult an effective amount of a compound as defined in claim 1.

10. A method of treating Alzheimer's disease, cerebral amyloid angiopathy, hereditary cerebral hemorrhage with amyloidosis, Dutch-type (HCHWA-D), multi-infarct dementia, dementia pugilistica or Down syndrome, which method comprises administering to an adult an effective amount of a compound as defined in claim 4.

11. A method of treating Alzheimer's disease, cerebral amyloid angiopathy, hereditary cerebral hemorrhage with amyloidosis, Dutch-type (HCHWA-D), multi-infarct dementia, dementia pugilistica or Down syndrome, which method comprises administering to an adult an effective amount of a compound as defined in claim 5.

12. A process for preparing a compound of formula I of claim 1, which process comprises:

a) reacting a compound of formula 7

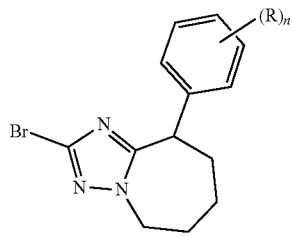

with a compound of formula 8

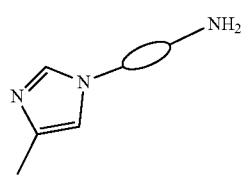

to form a compound of formula I and, optionally, converting the compound into a pharmaceutically acceptable acid addition salt;

or b) Cyclizing a compound of formula 14

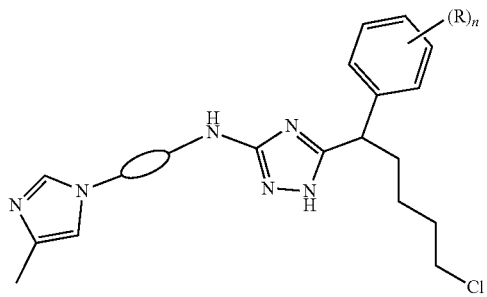

in the presence of KI and $K_2CO_3$ to form a compound of formula I and, optionally, converting the compound into a pharmaceutically acceptable acid addition salt.

13. A compound prepared by the process of claim 12.

* * * * *